US009486514B2

(12) United States Patent
Deora et al.

(10) Patent No.: US 9,486,514 B2
(45) Date of Patent: *Nov. 8, 2016

(54) BORDETELLA OUTER-MEMBRANE PROTEIN ANTIGENS AND METHODS OF MAKING AND USING THE SAME

(71) Applicant: Wake Forest University Health Sciences, Winston-Salem, NC (US)

(72) Inventors: Rajendar K. Deora, Winston-Salem, NC (US); Meenu Mishra, Winston-Salem, NC (US); Neelima Sukumar, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,665

(22) Filed: Feb. 3, 2016

(65) Prior Publication Data

US 2016/0144015 A1 May 26, 2016

Related U.S. Application Data

(63) Continuation of application No. 14/498,537, filed on Sep. 26, 2014, now Pat. No. 9,283,268, which is a continuation of application No. 12/680,823, filed as application No. PCT/US2008/012051 on Oct. 23, 2008, now Pat. No. 8,877,201.

(60) Provisional application No. 60/982,513, filed on Oct. 25, 2007.

(51) Int. Cl.
*C07K 14/235* (2006.01)
*A61K 39/02* (2006.01)
(Continued)

(52) U.S. Cl.
CPC .......... *A61K 39/099* (2013.01); *C07K 14/235* (2013.01); *C07K 16/1225* (2013.01);
(Continued)

(58) Field of Classification Search
CPC ............................. A61K 39/99; C07K 14/235
USPC ..................... 424/253.1, 254.1, 164.1, 242.1
See application file for complete search history.

(56) References Cited

U.S. PATENT DOCUMENTS

| 3,873,691 A | 3/1975 | Kasuga et al. |
| 4,016,253 A | 4/1977 | Switzer et al. |
| 4,225,583 A | 9/1980 | Switzer et al. |
| 4,888,169 A | 12/1989 | Brown et al. |
| 5,545,670 A | 8/1996 | Bissbort et al. |

(Continued)

FOREIGN PATENT DOCUMENTS

WO   WO 2005/032584 A2   4/2005

OTHER PUBLICATIONS

Weir, D. M. Handbook of experimental immunology, chapter 1, Immunochemistry, sections 8.14-8.15, pp. 1-4, Oxford: Blackwell Scientific 1986.*

(Continued)

*Primary Examiner* — Albert Navarro
*Assistant Examiner* — Ginny Portner
(74) *Attorney, Agent, or Firm* — Myers Bigel & Sibley, P.A.

(57) ABSTRACT

An isolated protein or peptide selected from the group consisting of *Bordetella* colonization factor A (BcfA) protein and antigenic fragments thereof is described, along with an isolated nucleic acid encoding the same, antibodies that bind to the same, methods of producing an immune response in a mammalian subject in need thereof by administering the proteins, peptides or antibodies, and pharmaceutical compositions comprising the same.

15 Claims, 4 Drawing Sheets

```
LTLGAVRTHPGTGVVTVTGKTGPGAKVRIDFPDGTFGDVVAGNGGDFTVASKGDVTA
SGPIVAIARDDDGRESPRRTVQYDDRVNGGGSGAPTVVLHTDGTNGRVTVSGKGRPG
DTIRVDFPDGTTKEVVAGPDGTYRVTSDRDMTAGDITVSGTDAKGNVGGPVKRPYHD
IFVPVPPTVEVATDSSSGRVTVSGKATPRAKVKVDFPGGTSKTVTADADGRYRATSD
GDVPGGDIVVTQTGMPGAAGKPVRRPYVDTVAPTPMKVTIDSMRTDGNSGVVTVTGY
TVGGSTVTVTFPDGTTAGTTANDRGKYTVTSTADIPAGPIRVSARGPRNQQGSATDH
YLDAWTKQTLLGGKIRLLRPVARLLLSPGSMTYTEIAKSFDGSSLDGIVARFEPANG
APPQTAALLAAIKLHDPNYRLESNKMFIYLDTMNSDPYNRVPNGDYPVTLVLEDKAT
GAREATTMVLKVTGSTYGKAPVVPGANGVLGTGPGPSLGGSLLIGGEGGLLGS
(SEQ ID NO:3)
```

(51) Int. Cl.
  C07K 16/12 (2006.01)
  G01N 33/569 (2006.01)
  A61K 39/00 (2006.01)
(52) U.S. Cl.
  CPC ... *G01N33/56911* (2013.01); *A61K 2039/505* (2013.01); *A61K 2039/55505* (2013.01); *A61K 2039/575* (2013.01); *G01N 2333/235* (2013.01)

(56) References Cited

U.S. PATENT DOCUMENTS

| | | | |
|---|---|---|---|
| 5,798,103 | A | 8/1998 | Mooi |
| 5,877,298 | A * | 3/1999 | Fahim ................. A61K 39/099 530/412 |
| 6,036,953 | A | 3/2000 | Ryan et al. |
| 6,582,705 | B1 | 6/2003 | Gueirard et al. |
| 7,049,423 | B2 | 5/2006 | Ryan |
| 7,101,987 | B2 * | 9/2006 | Vicari ..................... C07K 16/24 530/350 |
| 7,151,082 | B2 * | 12/2006 | Tracey ................. A61K 39/395 424/130.1 |
| 7,163,685 | B2 * | 1/2007 | Diamond ............. A61K 39/245 424/199.1 |
| 7,211,411 | B2 * | 5/2007 | Neefe .................. A61K 38/162 424/192.1 |
| 7,270,816 | B2 * | 9/2007 | Timans ................. C07K 14/54 424/139.1 |
| 7,479,283 | B1 | 1/2009 | Novotny |
| 7,659,388 | B2 | 2/2010 | Oh et al. |
| 8,507,201 | B2 * | 8/2013 | Cockerill, III ......... C12Q 1/689 435/6.1 |
| 8,669,091 | B2 | 3/2014 | Gentschev et al. |
| 8,877,201 | B2 * | 11/2014 | Deora .................. A61K 39/099 424/164.1 |
| 9,283,268 | B2 * | 3/2016 | Deora .................. A61K 39/099 |
| 2004/0029129 | A1 * | 2/2004 | Wang ..................... C07K 14/195 435/6.18 |
| 2004/0115210 | A1 | 6/2004 | Timmerman |
| 2006/0121450 | A1 | 6/2006 | Miller et al. |
| 2007/0116711 | A1 | 5/2007 | Castado et al. |
| 2008/0081770 | A1 | 4/2008 | Oh et al. |
| 2010/0028379 | A1 | 2/2010 | Tucker et al. |

OTHER PUBLICATIONS

Amara, A et al, Neuroscience Letters, Feb. 13, 1995, vol. 185(3), pp. 147-150, Molecular detection of methionine in rat brain using specific antibodies.*
Ellis, Chapter 29, pp. 568-575, Vaccines, 1991.*
Boslego, Chapter 17, pp. 211-223, Gonorrhea vaccines, Vaccines and Immunotherapy 1990.*
Dolby JM et al. The effect of the antigen which elicits the bactericidal antibody and of the mouse-protective antigen on the growth of Bordetella pertussis in the mouse brain. J. Hyg. Camb. 1975; 74: 71-83.
Sukumar N et al. Differential Bvg phase-dependent regulation and combinatorial role in pathogenesis of two Bordetella paralogs, BipA and BcfA. Journal of Bacteriology. May 2007; 189(10): 3695-3704.
Smith IM et al. Immunisation of pigs against experimental infection with Bordetella bronchiseptica. Veterinary Record. May 22, 1982; 110(21): 488-494.
Pittman M. Letter: Protective activity of whooping-cough convalescent serum and serum-IgA level in mice infected with Bordetella pertussis. Lancet. Jul. 17, 1976; 2(7922): 156.
Weir DM. Handbook of experimental immunology, chapter 1, Immunochemistry, sections 8.14-8.15, pp. 1-4, Oxford: Blackwell Scientific, 1986.
Mattoo S et al. Regulation of type III secretion in Bordetella. Molecular Microbiology; 2004; 52(4): 1201-1214.
NCBI Accession No. NP_886662, Adhesin Bordetella bronchiseptica RB50, pp. 1-3, deposited by Mattoo et al. 2004.
Parkhill J et al. Comparative analysis of the genome sequences of Bordetella pertussis, Bordetella parapertussis and Bordetella brochiseptica. Nature Genetics. Sep. 2003; 35(1): 32-40.
UniProt Accession No. Q7WR47, Oct. 1, 2003, one page, Bordetella bronchiseptica BB0110 putative adhesin.
Sebaihia M et al. Comparison of the genome sequence of the poultry pathogen Bordetella avium with those of B. brochiseptica, B. pertussis, and B. parapertussis reveals extensive diversity in surface structures associated with host interaction. Journal of Bacteriology. Aug. 2006; 188(16): 6002-6015.
Amara A et al. Molecular detection of methionine in rat brain using specific antibodies. Neuroscience Letters. Feb. 13, 1995; 185(3): 147-150.
Sukumar N et al. Differential Bvg phase-dependent regulation and combinatorial role in pathogenesis of two Bordetella paralogs, BipA and BcfA. Journal of Bacteriology. May 2007; 189(10); 3695-3704.
Mattoo S et al. Mechanisms of Bordetella pathogenesis. Front Biosci. Nov. 1, 2001; 1(6); pp. E168-E186.
Friedman LE et al. Short communication, Characterization of Bordetella bronchiseptica strains using phenotypic and genotypic markers. Veterinary Microbiology. 2006; 117: 313-320.
Fernandez J et al. Constitutive expression of bvgR-repressed factors is not detrimental to the Bordetella bronchiseptica-host interaction. Research in Microbiology. 2005; 156: 843-850.
Vergara-Irigaray N et al. Evaluation of the role of the Bvg intermediate phase in Bordetella pertussis during experimental respiratory infection. Infect. Immun. Feb. 2005; 73(2): 748-760.
Finn TM and Stevens LA. Tracheal colonization factor: a Bordetella pertussis secreted virulence determinant. Molecular Microbiology. 1995; 16(4): 625-634.
Leininger E et al. Inhibition of *Bordetella pertussis* filamentous hemagglutinin-mediated cell adherence with monoclonal antibodies. FEMS Microbiology Letters. 1993; 106: 31-38.
Vergara-Irigaray N et al. Evaluation of the role of the Bvg intermediate phase in *Bordetella pertussis* during experimental respiratory infection. Infection and Immunity. Feb. 2005; 73(2): 748-760.
NCBI database accession No. NP_886662 "Putative adhesion [Bordetella bronchiseptica RB50]", Jun. 7, 2007, 2 pp.
Sukumar N et al. Differential Bvg-phase-dependent regulation and role in pathogenesis of two *Bordetella* paralogs. Mid-Atlantic Microbial Pathogenesis Meeting, Feb. 11-13, 2007, Wintergreen, VA. Abstract.
Sukumar N et al. Differential Bvg-phase-dependent regulation and role in pathogenesis of two *Bordetella* paralogs, BipA and BcfA. ASM 107th General Meeting, May 21-25, 2007, Toronto, Canada. Abstract.
Sukumar N et al. Active and passive immunizations with *Bordetella* colonization factor A protect mice against respiratory challenge with *Bordetella bronchiseptica*. Infection and Immunity. Feb. 2009; 77(2): 885-895.
Zhao Z et al. Immunogenicity of recombinant protective antigen and efficacy against intranasal challenge with *Bordetella bronchiseptica*. Vaccine. 2009; 27: 2523-2528.
International Search Report and Written Opinion, PCT/US2008/012051, mailed Aug. 19, 2009.

* cited by examiner

```
GTGAAGCAAGCCATCCACGCCGTTGCGTTCCGCCATGATGCGCTCGCACGAGTCGGGCGTGTCCATCGG
CGCCGCGGCGCCGCCGCGCTGGCTGGCGTCTTGACGCTGCAAACCGTGGCGCCGGCATTTGCCCAGGGG
GCGCCGTCTTTCTCCGCCCGGCCCGCGCAGGCCGATCGCCAGGATGCCGCCGACAGCGCGATGCTGCGG
GTCGCGCAGACGGCGCGCCAATTGGCGCAACGGCAGGCTGCCGGTTCGCGCGCCTCGGCGCGCGTGGAC
GGCGACTTGCTGAAAGGACAGGCCGAGGCGCAGGCCAATGAGTTGCTGCAGGAAGGGGTGCGCCTGGCC
AACCAGACTGAATTGCCGTTCCTGCGCCGGTTGCAAGGCGGGGTGAATTATGACTTTTCGAACAAGGAC
CTGTCGTTGGATCTTCGTACCATCGACGAAGTGCATCGCGGCGAGCGCGACCGCGTCTTGCTGCAACTG
AGCGGCCACAATCGCAATCATCGTCCCACCGTCAACGGTGGCGTGGTGTTGCGCCATGCCTTGAACCAG
CACATGGCCGTGGGCGCCAACGCATTTCTTGATTACGAGTTCGGCAAGAACCATCTGCGCGGCTCGCTG
GGCGGAGAGGTCATTGCGCCGCAGTTCACGCTGTATGGCAACGTCTACGCGCCCATGTCGGGATGGAAA
GCGGCCAAGCGGGCCGAGCGCCGCGAAGAGCGGCCCGCCTCCGGCTGGGACGTTGGCGTGCGCCTGCAA
CCCGAGGCGCTGCCTGGCCTGGCAATCAAGGGCCAGTATTTCCGCTGGAGCGGCGCGGCCGTGGATTAC
TTCGACAACGGCCGTCCGCAGCGCAATGCGCGCGGCTATAAGTACGGCGTTGAGTACCGGCCCGTGCCG
TTGGTGGCGGTGGGCCTGGAACAGACCAAGGTGCTCGGCGGCGCGCGCCAGACCACTGTGCAGCTTGGC
GTCAATCTCAGCCTGGGCGAGCCCTTGTCCAGGCAGTTGCGGCACCAGTCCGGGCCGGCGTTCGACTTG
CAGGCCCGCATGGGCGAATTCGTCGAGCGTGAAAACCGCATCGTGCTTCAGACGCGCCGCAAGCACGTT
GTGTTGCCGCTGACGATCGCGCGCGTCGATACCGATCCGGCAACCGGGCGGATCACGGTAACCGGCGTC
ACCGAGCCGGGGCGCAGGTCAGCCTGGGGCTGCCCAATGGCGAAGTCGTGGTCGCGCAGGCCGATGGC
AGCGGAACCTACCGAGCGACGTCGGCGCGCGACATGGTGGGCGGCCCGGTGCGGGCTCGCGCAACGAAC
CGTCATGGCGACCGTAGCCGGAAGTCACGCACCATTACGTGGATGTCGCGGTCAAGGGCGAGGTACCG
CTGACGCTCGGCGCTGTGCGCACGCATCCTGGCACCGGCGTCGTGACCGTGACCGGCAAGACCGGGCCT
GGCGCCAAGGTGCGCATCGATTTTCCCGACGGTACGTTCGGTGATGTGGTCGCCGGCAATGGGGGCGAT
TTCACGGTCGCCTCGAAAGGCGATGTGACGGCCAGCGGCCCGATCGTGGCGATTGCCCGCGATGACGAC
GGGCGGGAAAGCCCCCGCCGTACTGTCCAGTACGACGACAGGGTCAATGGCGGTGGCTCGGGCGCGCCG
ACGGTGGTGCTGCATACCGACGGCACCAACGGTCGCGTGACGGTCAGCGGCAAAGGACGGCCCGGCGAT
ACGATCAGGGTGGACTTCCCCGACGGCACCACCAAGGAGGTGGTGGCGGGCCCGGACGGCACCTACCGC
GTCACGTCCGACCGCGACATGACGGCGGGCGACATAACGGTGTCCGGTACCGATGCCAAGGGCAACGTG
GGTGGTCCTGTCAAGCGTCCCTACCACGACATCTTCGTGCCCGTGCCGCCCACCGTGGAGGTGGCGACC
GACTCGTCCAGCGGCCGCGTCACGGTCAGCGGCAAGGCCACGCCGCGCGCCAAGGTCAAGGTCGATTTC
CCGGGCGGGACGTCCAAGACCGTCACCGCCGACGCCGACGGCCGCTATCGCGCGACCTCGGATGGCGAC
GTGCCTGGGGGCGACATCGTCGTCACGCAGACCGGGATGCCGGGCGCTGCGGGCAAGCCGGTGCGTCGA
CCGTATGTCGATACGGTGGCGCCGACGCCGATGAAAGTGACCATCGACAGCATGCGCACGGACGGCAAC
AGCGGCGTCGTGACGGTGACGGGCTACACGGTCGGCGGCTCCACGGTGACGGTGACCTTCCCCGACGGC
ACGACCGCCGGTACCACCGCCAATGACCGAGGCAAATACACGGTAACGTCGACCGCCGACATTCCTGCC
GGTCCGATCCGCGTCAGCGCGCGCGGACCGCGCAACCAGCAGGGCAGCGCGACGGACCATTACCTCGAT
GCGTGGACCAAGCAGACGCTGCTGGGCGGCAAGATTCGCCTTCTCCGGCCGGTCGCGAGGCTGTTGCTG
AGCCCGGGCAGCATGACATATACCGAAATCGCCAAGTCGTTCGATGGCAGTTCGCTCGACGGCATCGTG
GCACGGTTCGAGCCGGCAAACGGAGCACCGCCGCAGACGGCGGCGCTGCTGGCGGCGATCAAGCTGCAC
GATCCAAATTATCGGCTGGAGTCCAACAAGATGTTCATCTATCTCGACACCATGAACAGCGACCCGTAC
AACCGTGTTCCCAACGGCGATTATCCCGTCACGCTGGTTCTCGAGGACAAGGCCACCGGGGCGCGGGAG
GCGACCACCATGGTCCTGAAGGTGACCGGCAGTACCTATGGCAAAGCCCCGGTCGTCCCCGGCGCGAAT
GGTGTGCTTGGCACGGGCCCGGCCCGTCGTTGGCGGCAGTCTGCTGATCGGTGGCGAGGGCGGCCTG
CTGGGAAGCTGA (SEQ ID NO:1)
```

*FIG. 1*

MKQAIHAVAFRHDALARVGRVHRRRGAAALAGVLTLQTVAPAFAQGAPSFSARPAQA
DRQDAADSAMLRVAQTARQLAQRQAAGSRASARVDGDLLKGQAEAQANELLQEGVRL
ANQTELPFLRRLQGGVNYDFSNKDLSLDLRTIDEVHRGERDRVLLQLSGHNRHRPT
VNGGVVLRHALNQHMAVGANAFLDYEFGKNHLRGSLGGEVIAPQFTLYGNVYAPMSG
WKAAKRAERREERPASGWDVGVRLQPEALPGLAIKGQYFRWSGAAVDYFDNGRPQRN
ARGYKYGVEYRPVPLVAVGLEQTKVLGGARQTTVQLGVNLSLGEPLSRQLRHQSGPA
FDLQARMGEFVERENRIVLQTRRKHVVLPLTIARVDTDPATGRITVTGVTEPGAQVS
LGLPNGEVVVAQADGSGTYRATSARDMVGGPVRARATNRHGDRSREVTHHYVDVAVK
GEVPLTLGAVRTHPGTGVVTVTGKTGPGAKVRIDFPDGTFGDVVAGNGGDFTVASKG
DVTASGPIVAIARDDDGRESPRRTVQYDDRVNGGGSGAPTVVLHTDGTNGRVTVSGK
GRPGDTIRVDFPDGTTKEVVAGPDGTYRVTSDRDMTAGDITVSGTDAKGNVGGPVKR
PYHDIFVPVPPTVEVATDSSSGRVTVSGKATPRAKVKVDFPGGTSKTVTADADGRYR
ATSDGDVPGGDIVVTQTGMPGAAGKPVRRPYVDTVAPTPMKVTIDSMRTDGNSGVVT
VTGYTVGGSTVTVTFPDGTTAGTTANDRGKYTVTSTADIPAGPIRVSARGPRNQQGS
ATDHYLDAWTKQTLLGGKIRLLRPVARLLLSPGSMTYTEIAKSFDGSSLDGIVARFE
PANGAPPQTAALLAAIKLHDPNYRLESNKMFIYLDTMNSDPYNRVPNGDYPVTLVLE
DKATGAREATTMVLKVTGSTYGKAPVVPGANGVLGTGPGPSLGGSLLIGGEGGLLGS
(SEQ ID NO:2)

FIG. 2A

LTLGAVRTHPGTGVVTVTGKTGPGAKVRIDFPDGTFGDVVAGNGGDFTVASKGDVTA
SGPIVAIARDDDGRESPRRTVQYDDRVNGGGSGAPTVVLHTDGTNGRVTVSGKGRPG
DTIRVDFPDGTTKEVVAGPDGTYRVTSDRDMTAGDITVSGTDAKGNVGGPVKRPYHD
IFVPVPPTVEVATDSSSGRVTVSGKATPRAKVKVDFPGGTSKTVTADADGRYRATSD
GDVPGGDIVVTQTGMPGAAGKPVRRPYVDTVAPTPMKVTIDSMRTDGNSGVVTVTGY
TVGGSTVTVTFPDGTTAGTTANDRGKYTVTSTADIPAGPIRVSARGPRNQQGSATDH
YLDAWTKQTLLGGKIRLLRPVARLLLSPGSMTYTEIAKSFDGSSLDGIVARFEPANG
APPQTAALLAAIKLHDPNYRLESNKMFIYLDTMNSDPYNRVPNGDYPVTLVLEDKAT
GAREATTMVLKVTGSTYGKAPVVPGANGVLGTGPGPSLGGSLLIGGEGGLLGS
(SEQ ID NO:3)

FIG. 2B

LTLGAVRTHPGTGVVTVTGKTGPGAKVRIDFPDGTFGDVVAGNGGDFTVASKGDVTA
SGPIVAIARDDDGRESPRRTVQYDDRVNGGGSGAPTVVLHTDG (SEQ ID NO:4)

FIG. 2C

SKGDVTASGPIVAIARDDDGRESPRRTVQYDDRVNGGGSGAPTVVLHTDGTNGRVTV
SGKGRPGDTIRVDFPDGTTKEVVAGPDGTYRVTSDRDMTAGDI (SEQ ID NO:5)

FIG. 2D

TNGRVTVSGKGRPGDTIRVDFPDGTTKEVVAGPDGTYRVTSDRDMTAGDITVSGTDA
KGNVGGPVKRPYHDIFVPVPPTVEVATDSSSGRVTVSGKATPR (SEQ ID NO:6)

FIG. 2E

TVSGTDAKGNVGGPVKRPYHDIFVPVPPTVEVATDSSSGRVTVSGKATPRAKVKVDF
PGGTSKTVTADADGRYRATSDGDVPGGDIVVTQTGMPGAAGKP (SEQ ID NO:7)

FIG. 2F

AKVKVDFPGGTSKTVTADADGRYRATSDGDVPGGDIVVTQTGMPGAAGKPVRRPYVD
TVAPTPMKVTIDSMRTDGNSGVVTVTGYTVGGSTVTVTFPDGT (SEQ ID NO:8)

FIG. 2G

VRRPYVDTVAPTPMKVTIDSMRTDGNSGVVTVTGYTVGGSTVTVTFPDGTTAGTTAN
DRGKYTVTSTADIPAGPIRVSARGPRNQQGSATDHYLDAWTKQ (SEQ ID NO:9)

FIG. 2H

TAGTTANDRGKYTVTSTADIPAGPIRVSARGPRNQQGSATDHYLDAWTKQTLLGGKI
RLLRPVARLLLSPGSMTYTEIAKSFDGSSLDGIVARFEPANGA
                    (SEQ ID NO:10)

FIG. 2I

TLLGGKIRLLRPVARLLLSPGSMTYTEIAKSFDGSSLDGIVARFEPANGAPPQTAAL
LAAIKLHDPNYRLESNKMFIYLDTMNSDPYNRVPNGDYPVTLV
                    (SEQ ID NO:11)

FIG. 2J

PPQTAALLAAIKLHDPNYRLESNKMFIYLDTMNSDPYNRVPNGDYPVTLVLEDKATG
AREATTMVLKVTGSTYGKAPVVPGANGVLGTGPGPSLGGSLLI
                    (SEQ ID NO:12)

FIG. 2K

LEDKATGAREATTMVLKVTGSTYGKAPVVPGANGVLGTGPGPSLGGSLLIGGEGGLL
GS (SEQ ID NO:13)

FIG. 2L

SEQUENCE LISTING

```
<160> NUMBER OF SEQ ID NOS: 85

<210> SEQ ID NO 1
<211> LENGTH: 2910
<212> TYPE: DNA
<213> ORGANISM: Bordetella bronchiseptica

<400> SEQUENCE: 1
gtgaagcaag ccatccacgc cgttgcgttc cgccatgatg cgctcgcacg agtcgggcgt     60
gtccatcggc gccgcggcgc cgccgcgctg gctggcgtct tgacgctgca aaccgtggcg    120
ccggcatttg cccagggggc gccgtctttc tccgcccggc ccgcgcaggc cgatcgccag    180
gatgccgccg acagcgcgat gctgcgggtc gcgcagacgg cgcgccaatt ggcgcaacgg    240
caggctgccg gttcgcgcgc ctcggcgcgc gtggacggcg acttgctgaa aggacaggcc    300
gaggcgcagg ccaatgagtt gctgcaggaa ggggtgcgcc tggccaacca gactgaattg    360
ccgttcctgc gccggttgca aggcggggtg aattatgact tttcgaacaa ggacctgtcg    420
ttggatcttc gtaccatcga cgaagtgcat cgcggcgagc gcgaccgcgt cttgctgcaa    480
ctgagcggcc acaatcgcaa tcatcgtccc accgtcaacg gtggcgtggt gttgcgccat    540
gccttgaacc agcacatggc cgtgggcgcc aacgcatttc ttgattacga gttcggcaag    600
aaccatctgc gcggctcgct gggcggagag gtcattgcgc cgcagttcac gctgtatggc    660
aacgtctacg cgcccatgtc gggatggaaa gcggccaagc gggccgagcg ccgcgaagag    720
cggcccgcct ccggctggga cgttggcgtg cgcctgcaac ccgaggcgct gcctggcctg    780
gcaatcaagg gccagtattt ccgctggagc ggcgcggccg tggattactt cgacaacggc    840
cgtccgcagc gcaatgcgcg cggctataag tacggcgttg agtaccggcc cgtgccgttg    900
gtggcggtgg gcctggaaca gaccaaggtg ctcggcggcg cgcgccagac cactgtgcag    960
cttggcgtca atctcagcct gggcgagccc ttgtccaggc agttgcggca ccagtccggg   1020
ccggcgttcg acttgcaggc ccgcatgggc gaattcgtcg agcgtgaaaa ccgcatcgtg   1080
cttcagacgc gccgcaagca cgttgtgttg ccgctgacga tcgcgcgcgt cgataccgat   1140
ccggcaaccg ggcggatcac ggtaaccggc gtcaccgagc cgggggcgca ggtcagcctg   1200
gggctgccca atggcgaagt cgtggtcgcg caggccgatg gcagcggaac ctaccgagcg   1260
acgtcggcgc gcgacatggt gggcggcccg gtgcgggctc gcgcaacgaa ccgtcatggc   1320
gaccgtagcc gggaagtcac gcaccattac gtggatgtcg cggtcaaggg cgaggtaccg   1380
ctgacgctcg gcgctgtgcg cacgcatcct ggcaccggcg tcgtgaccgt gaccggcaag   1440
accgggcctg gcgccaaggt gcgcatcgat tttcccgacg gtacgttcgg tgatgtggtc   1500
gccggcaatg gggcgatttt cacggtcgcc tcgaaaggcg atgtgacggc cagcggcccg   1560
atcgtggcga ttgcccgcga tgacgacggg cgggaaagcc cccgccgtac tgtccagtac   1620
gacgacaggg tcaatggcgg tggctcgggc gcgccgacgg tggtgctgca taccgacggc   1680
accaacggtc gcgtgacggt cagcggcaaa ggacggcccg gcgatacgat cagggtggac   1740
ttccccgacg gcaccaccaa ggaggtggtg gcgggcccgg acggcaccta ccgcgtcacg   1800
tccgaccgcg acatgacggc gggcgacata acggtgtccg gtaccgatgc caagggcaac   1860
```

-continued

```
gtgggtggtc ctgtcaagcg tccctaccac gacatcttcg tgcccgtgcc gcccaccgtg    1920
gaggtggcga ccgactcgtc cagcggccgc gtcacggtca gcggcaaggc cacgccgcgc    1980
gccaaggtca aggtcgattt cccgggcggg acgtccaaga ccgtcaccgc cgacgccgac    2040
ggccgctatc gcgcgacctc ggatggcgac gtgcctgggg cgacatcgt cgtcacgcag     2100
accgggatgc cgggcgctgc gggcaagccg gtgcgtcgac cgtatgtcga tacggtggcg    2160
ccgacgccga tgaaagtgac catcgacagc atgcgcacgg acggcaacag cggcgtcgtg    2220
acggtgacgg gctacacggt cggcggctcc acggtgacgg tgaccttccc cgacggcacg    2280
accgccggta ccaccgccaa tgaccgaggc aaatacacgg taacgtcgac cgccgacatt    2340
cctgccggtc cgatccgcgt cagcgcgcgc ggaccgcgca accagcaggg cagcgcgacg    2400
gaccattacc tcgatgcgtg gaccaagcag acgctgctgg cggcaagat cgccttctc     2460
cggccggtcg cgaggctgtt gctgagcccg ggcagcatga catataccga aatcgccaag    2520
tcgttcgatg gcagttcgct cgacggcatc gtggcacggt tcgagccggc aaacggagca    2580
ccgccgcaga cggcggcgct gctggcggcg atcaagctgc acgatccaaa ttatcggctg    2640
gagtccaaca agatgttcat ctatctcgac accatgaaca gcgacccgta caaccgtgtt    2700
cccaacggcg attatcccgt cacgctggtt ctcgaggaca aggccaccgg ggcgcgggag    2760
gcgaccacca tggtcctgaa ggtgaccggc agtacctatg caaagcccc ggtcgtcccc     2820
ggcgcgaatg tgtgcttgg cacggggccc ggcccgtcgt tgggcggcag tctgctgatc     2880
ggtggcgagg gcggcctgct gggaagctga                                     2910
```

<210> SEQ ID NO 2
<211> LENGTH: 969
<212> TYPE: PRT
<213> ORGANISM: Bordetella bronchiseptica

<400> SEQUENCE: 2

```
Met Lys Gln Ala Ile His Ala Val Ala Phe Arg His Asp Ala Leu Ala
1               5                   10                  15

Arg Val Gly Arg Val His Arg Arg Gly Ala Ala Leu Ala Gly
            20                  25                  30

Val Leu Thr Leu Gln Thr Val Ala Pro Ala Phe Ala Gln Gly Ala Pro
        35                  40                  45

Ser Phe Ser Ala Arg Pro Ala Gln Ala Asp Arg Gln Asp Ala Ala Asp
    50                  55                  60

Ser Ala Met Leu Arg Val Ala Gln Thr Ala Arg Gln Leu Ala Gln Arg
65                  70                  75                  80

Gln Ala Ala Gly Ser Arg Ala Ser Ala Arg Val Asp Gly Asp Leu Leu
                85                  90                  95

Lys Gly Gln Ala Glu Ala Gln Ala Asn Glu Leu Leu Gln Glu Gly Val
            100                 105                 110

Arg Leu Ala Asn Gln Thr Glu Leu Pro Phe Leu Arg Arg Leu Gln Gly
        115                 120                 125

Gly Val Asn Tyr Asp Phe Ser Asn Lys Asp Leu Ser Leu Asp Leu Arg
    130                 135                 140

Thr Ile Asp Glu Val His Arg Gly Glu Arg Asp Arg Val Leu Leu Gln
145                 150                 155                 160

Leu Ser Gly His Asn Arg Asn His Arg Pro Thr Val Asn Gly Gly Val
                165                 170                 175

Val Leu Arg His Ala Leu Asn Gln His Met Ala Val Gly Ala Asn Ala
            180                 185                 190
```

-continued

```
Phe Leu Asp Tyr Glu Phe Gly Lys Asn His Leu Arg Gly Ser Leu Gly
            195                 200                 205
Gly Glu Val Ile Ala Pro Gln Phe Thr Leu Tyr Gly Asn Val Tyr Ala
210                 215                 220
Pro Met Ser Gly Trp Lys Ala Ala Lys Arg Ala Glu Arg Arg Glu Glu
225                 230                 235                 240
Arg Pro Ala Ser Gly Trp Asp Val Gly Val Arg Leu Gln Pro Glu Ala
                245                 250                 255
Leu Pro Gly Leu Ala Ile Lys Gly Gln Tyr Phe Arg Trp Ser Gly Ala
            260                 265                 270
Ala Val Asp Tyr Phe Asp Asn Gly Arg Pro Gln Arg Asn Ala Arg Gly
        275                 280                 285
Tyr Lys Tyr Gly Val Glu Tyr Arg Pro Val Pro Leu Ala Val Gly
    290                 295                 300
Leu Glu Gln Thr Lys Val Leu Gly Gly Ala Arg Gln Thr Thr Val Gln
305                 310                 315                 320
Leu Gly Val Asn Leu Ser Leu Gly Glu Pro Leu Ser Arg Gln Leu Arg
                325                 330                 335
His Gln Ser Gly Pro Ala Phe Asp Leu Gln Ala Arg Met Gly Glu Phe
            340                 345                 350
Val Glu Arg Glu Asn Arg Ile Val Leu Gln Thr Arg Arg Lys His Val
        355                 360                 365
Val Leu Pro Leu Thr Ile Ala Arg Val Asp Thr Asp Pro Ala Thr Gly
    370                 375                 380
Arg Ile Thr Val Thr Gly Val Thr Glu Pro Gly Ala Gln Val Ser Leu
385                 390                 395                 400
Gly Leu Pro Asn Gly Glu Val Val Ala Gln Ala Asp Gly Ser Gly
                405                 410                 415
Thr Tyr Arg Ala Thr Ser Ala Arg Asp Met Val Gly Gly Pro Val Arg
            420                 425                 430
Ala Arg Ala Thr Asn Arg His Gly Asp Arg Ser Arg Glu Val Thr His
        435                 440                 445
His Tyr Val Asp Val Ala Val Lys Gly Glu Val Pro Leu Thr Leu Gly
    450                 455                 460
Ala Val Arg Thr His Pro Gly Thr Gly Val Val Thr Val Thr Gly Lys
465                 470                 475                 480
Thr Gly Pro Gly Ala Lys Val Arg Ile Asp Phe Pro Asp Gly Thr Phe
                485                 490                 495
Gly Asp Val Val Ala Gly Asn Gly Gly Asp Phe Thr Val Ala Ser Lys
            500                 505                 510
Gly Asp Val Thr Ala Ser Gly Pro Ile Val Ala Ile Ala Arg Asp Asp
        515                 520                 525
Asp Gly Arg Glu Ser Pro Arg Arg Thr Val Gln Tyr Asp Asp Arg Val
    530                 535                 540
Asn Gly Gly Gly Ser Gly Ala Pro Thr Val Val Leu His Thr Asp Gly
545                 550                 555                 560
Thr Asn Gly Arg Val Thr Val Ser Gly Lys Gly Arg Pro Gly Asp Thr
                565                 570                 575
Ile Arg Val Asp Phe Pro Asp Gly Thr Thr Lys Glu Val Val Ala Gly
            580                 585                 590
Pro Asp Gly Thr Tyr Arg Val Thr Ser Asp Arg Asp Met Thr Ala Gly
        595                 600                 605
```

Asp Ile Thr Val Ser Gly Thr Asp Ala Lys Gly Asn Val Gly Gly Pro
610                 615                 620

Val Lys Arg Pro Tyr His Asp Ile Phe Val Pro Val Pro Pro Thr Val
625                 630                 635                 640

Glu Val Ala Thr Asp Ser Ser Ser Gly Arg Val Thr Val Ser Gly Lys
                645                 650                 655

Ala Thr Pro Arg Ala Lys Val Lys Val Asp Phe Pro Gly Gly Thr Ser
                660                 665                 670

Lys Thr Val Thr Ala Asp Ala Asp Gly Arg Tyr Arg Ala Thr Ser Asp
                675                 680                 685

Gly Asp Val Pro Gly Gly Asp Ile Val Val Thr Gln Thr Gly Met Pro
690                 695                 700

Gly Ala Ala Gly Lys Pro Val Arg Arg Pro Tyr Val Asp Thr Val Ala
705                 710                 715                 720

Pro Thr Pro Met Lys Val Thr Ile Asp Ser Met Arg Thr Asp Gly Asn
                725                 730                 735

Ser Gly Val Val Thr Val Thr Gly Tyr Thr Val Gly Gly Ser Thr Val
                740                 745                 750

Thr Val Thr Phe Pro Asp Gly Thr Thr Ala Gly Thr Thr Ala Asn Asp
                755                 760                 765

Arg Gly Lys Tyr Thr Val Thr Ser Thr Ala Asp Ile Pro Ala Gly Pro
770                 775                 780

Ile Arg Val Ser Ala Arg Gly Pro Arg Asn Gln Gln Gly Ser Ala Thr
785                 790                 795                 800

Asp His Tyr Leu Asp Ala Trp Thr Lys Gln Thr Leu Leu Gly Gly Lys
                805                 810                 815

Ile Arg Leu Leu Arg Pro Val Ala Arg Leu Leu Ser Pro Gly Ser
                820                 825                 830

Met Thr Tyr Thr Glu Ile Ala Lys Ser Phe Asp Gly Ser Ser Leu Asp
                835                 840                 845

Gly Ile Val Ala Arg Phe Glu Pro Ala Asn Gly Ala Pro Pro Gln Thr
850                 855                 860

Ala Ala Leu Leu Ala Ala Ile Lys Leu His Asp Pro Asn Tyr Arg Leu
865                 870                 875                 880

Glu Ser Asn Lys Met Phe Ile Tyr Leu Asp Thr Met Asn Ser Asp Pro
                885                 890                 895

Tyr Asn Arg Val Pro Asn Gly Asp Tyr Pro Val Thr Leu Val Leu Glu
                900                 905                 910

Asp Lys Ala Thr Gly Ala Arg Glu Ala Thr Thr Met Val Leu Lys Val
                915                 920                 925

Thr Gly Ser Thr Tyr Gly Lys Ala Pro Val Val Pro Gly Ala Asn Gly
930                 935                 940

Val Leu Gly Thr Gly Pro Gly Pro Ser Leu Gly Gly Ser Leu Leu Ile
945                 950                 955                 960

Gly Gly Glu Gly Gly Leu Leu Gly Ser
                965

<210> SEQ ID NO 3
<211> LENGTH: 509
<212> TYPE: PRT
<213> ORGANISM: Bordetella bronchiseptica -continued

```
<400> SEQUENCE: 3

Leu Thr Leu Gly Ala Val Arg Thr His Pro Gly Thr Val Val Thr
1               5                   10                  15

Val Thr Gly Lys Thr Gly Pro Gly Ala Lys Val Arg Ile Asp Phe Pro
                20                  25                  30

Asp Gly Thr Phe Gly Asp Val Ala Gly Asn Gly Asp Phe Thr
                35                  40                  45

Val Ala Ser Lys Gly Asp Val Thr Ala Ser Gly Pro Ile Val Ala Ile
50                  55                  60

Ala Arg Asp Asp Gly Arg Glu Ser Pro Arg Arg Thr Val Gln Tyr
65                  70                  75                  80

Asp Asp Arg Val Asn Gly Gly Ser Gly Ala Pro Thr Val Leu
                85                  90                  95

His Thr Asp Gly Thr Asn Gly Arg Val Thr Val Ser Gly Lys Gly Arg
                100                 105                 110

Pro Gly Asp Thr Ile Arg Val Asp Phe Pro Asp Gly Thr Thr Lys Glu
                115                 120                 125

Val Val Ala Gly Pro Asp Gly Thr Tyr Arg Val Thr Ser Asp Arg Asp
                130                 135                 140

Met Thr Ala Gly Asp Ile Thr Val Ser Gly Thr Asp Ala Lys Gly Asn
145                 150                 155                 160

Val Gly Gly Pro Val Lys Arg Pro Tyr His Asp Ile Phe Val Pro Val
                165                 170                 175

Pro Pro Thr Val Glu Val Ala Thr Asp Ser Ser Ser Gly Arg Val Thr
                180                 185                 190

Val Ser Gly Lys Ala Thr Pro Arg Ala Lys Val Lys Val Asp Phe Pro
                195                 200                 205

Gly Gly Thr Ser Lys Thr Val Thr Ala Asp Ala Asp Gly Arg Tyr Arg
                210                 215                 220

Ala Thr Ser Asp Gly Asp Val Pro Gly Gly Asp Ile Val Val Thr Gln
225                 230                 235                 240

Thr Gly Met Pro Gly Ala Ala Gly Lys Pro Val Arg Arg Pro Tyr Val
                245                 250                 255

Asp Thr Val Ala Pro Thr Pro Met Lys Val Thr Ile Asp Ser Met Arg
                260                 265                 270

Thr Asp Gly Asn Ser Gly Val Val Thr Val Thr Gly Tyr Thr Val Gly
                275                 280                 285

Gly Ser Thr Val Thr Val Thr Phe Pro Asp Gly Thr Thr Ala Gly Thr
                290                 295                 300

Thr Ala Asn Asp Arg Gly Lys Tyr Thr Val Thr Ser Thr Ala Asp Ile
305                 310                 315                 320

Pro Ala Gly Pro Ile Arg Val Ser Ala Arg Gly Pro Arg Asn Gln Gln
                325                 330                 335

Gly Ser Ala Thr Asp His Tyr Leu Asp Ala Trp Thr Lys Gln Thr Leu
                340                 345                 350

Leu Gly Gly Lys Ile Arg Leu Leu Arg Pro Val Ala Arg Leu Leu Leu
                355                 360                 365

Ser Pro Gly Ser Met Thr Tyr Thr Glu Ile Ala Lys Ser Phe Asp Gly
                370                 375                 380

Ser Ser Leu Asp Gly Ile Val Ala Arg Phe Glu Pro Ala Asn Gly Ala
385                 390                 395                 400

Pro Pro Gln Thr Ala Ala Leu Leu Ala Ala Ile Lys Leu His Asp Pro
                405                 410                 415
```

Asn Tyr Arg Leu Glu Ser Asn Lys Met Phe Ile Tyr Leu Asp Thr Met
            420                 425                 430

Asn Ser Asp Pro Tyr Asn Arg Val Pro Asn Gly Asp Tyr Pro Val Thr
        435                 440                 445

Leu Val Leu Glu Asp Lys Ala Thr Gly Ala Arg Glu Ala Thr Thr Met
    450                 455                 460

Val Leu Lys Val Thr Gly Ser Thr Tyr Gly Lys Ala Pro Val Val Pro
465                 470                 475                 480

Gly Ala Asn Gly Val Leu Gly Thr Gly Pro Gly Pro Ser Leu Gly Gly
                485                 490                 495

Ser Leu Leu Ile Gly Gly Glu Gly Gly Leu Leu Gly Ser
            500                 505

<210> SEQ ID NO 4
<211> LENGTH: 100
<212> TYPE: PRT
<213> ORGANISM: Bordetella bronchiseptica

<400> SEQUENCE: 4

Leu Thr Leu Gly Ala Val Arg Thr His Pro Gly Thr Gly Val Val Thr
1               5                   10                  15

Val Thr Gly Lys Thr Gly Pro Gly Ala Lys Val Arg Ile Asp Phe Pro
            20                  25                  30

Asp Gly Thr Phe Gly Asp Val Val Ala Gly Asn Gly Gly Asp Phe Thr
        35                  40                  45

Val Ala Ser Lys Gly Asp Val Thr Ala Ser Gly Pro Ile Val Ala Ile
    50                  55                  60

Ala Arg Asp Asp Gly Arg Glu Ser Pro Arg Thr Val Gln Tyr
65                  70                  75                  80

Asp Asp Arg Val Asn Gly Gly Ser Gly Ala Pro Thr Val Val Leu
                85                  90                  95

His Thr Asp Gly
            100

<210> SEQ ID NO 5
<211> LENGTH: 100
<212> TYPE: PRT
<213> ORGANISM: Bordetella bronchiseptica

<400> SEQUENCE: 5

Ser Lys Gly Asp Val Thr Ala Ser Gly Pro Ile Val Ala Ile Ala Arg
1               5                   10                  15

Asp Asp Asp Gly Arg Glu Ser Pro Arg Arg Thr Val Gln Tyr Asp Asp
            20                  25                  30

Arg Val Asn Gly Gly Ser Gly Ala Pro Thr Val Val Leu His Thr
        35                  40                  45

Asp Gly Thr Asn Gly Arg Val Thr Val Ser Gly Lys Gly Arg Pro Gly
    50                  55                  60

Asp Thr Ile Arg Val Asp Phe Pro Asp Gly Thr Thr Lys Glu Val Val
65                  70                  75                  80

Ala Gly Pro Asp Gly Thr Tyr Arg Val Thr Ser Asp Arg Asp Met Thr
                85                  90                  95

Ala Gly Asp Ile
            100

<210> SEQ ID NO 6
<211> LENGTH: 100
<212> TYPE: PRT
<213> ORGANISM: Bordetella bronchiseptica

<400> SEQUENCE: 6

Ser Lys Gly Asp Val Thr Ala Ser Gly Pro Ile Val Ala Ile Ala Arg
1               5                   10                  15

Asp Asp Asp Gly Arg Glu Ser Pro Arg Arg Thr Val Gln Tyr Asp Asp
            20                  25                  30

Arg Val Asn Gly Gly Ser Gly Ala Pro Thr Val Val Leu His Thr
        35                  40                  45

Asp Gly Thr Asn Gly Arg Val Thr Val Ser Gly Lys Gly Arg Pro Gly
    50                  55                  60

Asp Thr Ile Arg Val Asp Phe Pro Asp Gly Thr Thr Lys Glu Val Val
65                  70                  75                  80

Ala Gly Pro Asp Gly Thr Tyr Arg Val Thr Ser Asp Arg Asp Met Thr
                85                  90                  95

Ala Gly Asp Ile
            100

<210> SEQ ID NO 7
<211> LENGTH: 100
<212> TYPE: PRT
<213> ORGANISM: Bordetella bronchiseptica

<400> SEQUENCE: 7

Ser Lys Gly Asp Val Thr Ala Ser Gly Pro Ile Val Ala Ile Ala Arg
1               5                   10                  15

Asp Asp Asp Gly Arg Glu Ser Pro Arg Arg Thr Val Gln Tyr Asp Asp
            20                  25                  30

Arg Val Asn Gly Gly Ser Gly Ala Pro Thr Val Val Leu His Thr
        35                  40                  45

Asp Gly Thr Asn Gly Arg Val Thr Val Ser Gly Lys Gly Arg Pro Gly
    50                  55                  60

Asp Thr Ile Arg Val Asp Phe Pro Asp Gly Thr Thr Lys Glu Val Val
65                  70                  75                  80

Ala Gly Pro Asp Gly Thr Tyr Arg Val Thr Ser Asp Arg Asp Met Thr
                85                  90                  95

Ala Gly Asp Ile
            100

<210> SEQ ID NO 8
<211> LENGTH: 100
<212> TYPE: PRT
<213> ORGANISM: Bordetella bronchiseptica

<400> SEQUENCE: 8

Ala Lys Val Lys Val Asp Phe Pro Gly Gly Thr Ser Lys Thr Val Thr
1               5                   10                  15

Ala Asp Ala Asp Gly Arg Tyr Arg Ala Thr Ser Asp Gly Asp Val Pro
            20                  25                  30

Gly Gly Asp Ile Val Val Thr Gln Thr Gly Met Pro Gly Ala Ala Gly
        35                  40                  45

Lys Pro Val Arg Arg Pro Tyr Val Asp Thr Val Ala Pro Thr Pro Met
    50                  55                  60

Lys Val Thr Ile Asp Ser Met Arg Thr Asp Gly Asn Ser Gly Val Val
65                  70                  75                  80

```
Thr Val Thr Gly Tyr Thr Val Gly Gly Ser Thr Val Thr Val Thr Phe
                85                  90                  95

Pro Asp Gly Thr
            100

<210> SEQ ID NO 9
<211> LENGTH: 100
<212> TYPE: PRT
<213> ORGANISM: Bordetella bronchiseptica

<400> SEQUENCE: 9

Val Arg Arg Pro Tyr Val Asp Thr Val Ala Pro Thr Pro Met Lys Val
1               5                   10                  15

Thr Ile Asp Ser Met Arg Thr Asp Gly Asn Ser Gly Val Val Thr Val
                20                  25                  30

Thr Gly Tyr Thr Val Gly Gly Ser Thr Val Thr Val Thr Phe Pro Asp
            35                  40                  45

Gly Thr Thr Ala Gly Thr Thr Ala Asn Asp Arg Gly Lys Tyr Thr Val
    50                  55                  60

Thr Ser Thr Ala Asp Ile Pro Ala Gly Pro Ile Arg Val Ser Ala Arg
65                  70                  75                  80

Gly Pro Arg Asn Gln Gln Gly Ser Ala Thr Asp His Tyr Leu Asp Ala
                85                  90                  95

Trp Thr Lys Gln
            100

<210> SEQ ID NO 10
<211> LENGTH: 100
<212> TYPE: PRT
<213> ORGANISM: Bordetella bronchiseptica

<400> SEQUENCE: 10

Thr Ala Gly Thr Thr Ala Asn Asp Arg Gly Lys Tyr Thr Val Thr Ser
1               5                   10                  15

Thr Ala Asp Ile Pro Ala Gly Pro Ile Arg Val Ser Ala Arg Gly Pro
                20                  25                  30

Arg Asn Gln Gln Gly Ser Ala Thr Asp His Tyr Leu Asp Ala Trp Thr
            35                  40                  45

Lys Gln Thr Leu Leu Gly Gly Lys Ile Arg Leu Leu Arg Pro Val Ala
    50                  55                  60

Arg Leu Leu Leu Ser Pro Gly Ser Met Thr Tyr Thr Glu Ile Ala Lys
65                  70                  75                  80

Ser Phe Asp Gly Ser Ser Leu Asp Gly Ile Val Ala Arg Phe Glu Pro
                85                  90                  95

Ala Asn Gly Ala
            100

<210> SEQ ID NO 11
<211> LENGTH: 100
<212> TYPE: PRT
<213> ORGANISM: Bordetella bronchiseptica

<400> SEQUENCE: 11

Thr Leu Leu Gly Gly Lys Ile Arg Leu Leu Arg Pro Val Ala Arg Leu
1               5                   10                  15

Leu Leu Ser Pro Gly Ser Met Thr Tyr Thr Glu Ile Ala Lys Ser Phe
                20                  25                  30
```

```
Asp Gly Ser Ser Leu Asp Gly Ile Val Ala Arg Phe Glu Pro Ala Asn
            35                  40                  45

Gly Ala Pro Pro Gln Thr Ala Ala Leu Leu Ala Ala Ile Lys Leu His
        50                  55                  60

Asp Pro Asn Tyr Arg Leu Glu Ser Asn Lys Met Phe Ile Tyr Leu Asp
65                  70                  75                  80

Thr Met Asn Ser Asp Pro Tyr Asn Arg Val Pro Asn Gly Asp Tyr Pro
                85                  90                  95

Val Thr Leu Val
            100

<210> SEQ ID NO 12
<211> LENGTH: 100
<212> TYPE: PRT
<213> ORGANISM: Bordetella bronchiseptica

<400> SEQUENCE: 12

Pro Pro Gln Thr Ala Ala Leu Leu Ala Ala Ile Lys Leu His Asp Pro
1               5                   10                  15

Asn Tyr Arg Leu Glu Ser Asn Lys Met Phe Ile Tyr Leu Asp Thr Met
            20                  25                  30

Asn Ser Asp Pro Tyr Asn Arg Val Pro Asn Gly Asp Tyr Pro Val Thr
        35                  40                  45

Leu Val Leu Glu Asp Lys Ala Thr Gly Ala Arg Glu Ala Thr Thr Met
    50                  55                  60

Val Leu Lys Val Thr Gly Ser Thr Tyr Gly Lys Ala Pro Val Val Pro
65                  70                  75                  80

Gly Ala Asn Gly Val Leu Gly Thr Gly Pro Gly Pro Ser Leu Gly Gly
                85                  90                  95

Ser Leu Leu Ile
            100

<210> SEQ ID NO 13
<211> LENGTH: 59
<212> TYPE: PRT
<213> ORGANISM: Bordetella bronchiseptica

<400> SEQUENCE: 13

Leu Glu Asp Lys Ala Thr Gly Ala Arg Glu Ala Thr Thr Met Val Leu
1               5                   10                  15

Lys Val Thr Gly Ser Thr Tyr Gly Lys Ala Pro Val Val Pro Gly Ala
            20                  25                  30

Asn Gly Val Leu Gly Thr Gly Pro Gly Pro Ser Leu Gly Gly Ser Leu
        35                  40                  45

Leu Ile Gly Gly Glu Gly Gly Leu Leu Gly Ser
    50                  55

<210> SEQ ID NO 14
<211> LENGTH: 11
<212> TYPE: PRT
<213> ORGANISM: Bordetella bronchiseptica

<400> SEQUENCE: 14

Gly Asp Tyr Pro Val Thr Leu Val Leu Glu Asp
1               5                   10
```

```
<210> SEQ ID NO 15
<211> LENGTH: 24
<212> TYPE: PRT
<213> ORGANISM: Bordetella bronchiseptica

<400> SEQUENCE: 15

Gly Gly Pro Val Lys Arg Pro Tyr His Asp Ile Phe Val Pro Val Pro
 1               5                  10                  15

Pro Thr Val Glu Val Ala Thr Asp
            20

<210> SEQ ID NO 16
<211> LENGTH: 8
<212> TYPE: PRT
<213> ORGANISM: Bordetella bronchiseptica

<400> SEQUENCE: 16

Ala Pro Thr Val Val Leu His Thr
 1               5

<210> SEQ ID NO 17
<211> LENGTH: 21
<212> TYPE: PRT
<213> ORGANISM: Bordetella bronchiseptica

<400> SEQUENCE: 17

Gln Thr Leu Leu Gly Gly Lys Ile Arg Leu Leu Arg Pro Val Ala Arg
 1               5                  10                  15

Leu Leu Leu Ser Pro
            20

<210> SEQ ID NO 18
<211> LENGTH: 9
<212> TYPE: PRT
<213> ORGANISM: Bordetella bronchiseptica

<400> SEQUENCE: 18

Ser Gly Val Val Thr Val Thr Gly Tyr
 1               5

<210> SEQ ID NO 19
<211> LENGTH: 16
<212> TYPE: PRT
<213> ORGANISM: Bordetella bronchiseptica

<400> SEQUENCE: 19

Pro Gln Thr Ala Ala Leu Leu Ala Ala Ile Lys Leu His Asp Pro Asn
 1               5                  10                  15

<210> SEQ ID NO 20
<211> LENGTH: 12
<212> TYPE: PRT
<213> ORGANISM: Bordetella bronchiseptica

<400> SEQUENCE: 20

Gly Lys Ala Pro Val Val Pro Gly Ala Asn Gly Val
 1               5                  10

<210> SEQ ID NO 21
<211> LENGTH: 22
<212> TYPE: PRT
<213> ORGANISM: Bordetella bronchiseptica
```

<400> SEQUENCE: 21

Gly Lys Pro Val Arg Arg Pro Tyr Val Asp Thr Val Ala Pro Thr Pro
1               5                   10                  15
Met Lys Val Thr Ile Asp
            20

<210> SEQ ID NO 22
<211> LENGTH: 8
<212> TYPE: PRT
<213> ORGANISM: Bordetella bronchiseptica

<400> SEQUENCE: 22

Gly Thr Gly Val Val Thr Val Thr
1               5

<210> SEQ ID NO 23
<211> LENGTH: 9
<212> TYPE: PRT
<213> ORGANISM: Bordetella bronchiseptica

<400> SEQUENCE: 23

Ala Ser Gly Pro Ile Val Ala Ile Ala
1               5

<210> SEQ ID NO 24
<211> LENGTH: 9
<212> TYPE: PRT
<213> ORGANISM: Bordetella bronchiseptica

<400> SEQUENCE: 24

Thr Met Val Leu Lys Val Thr Gly Ser
1               5

<210> SEQ ID NO 25
<211> LENGTH: 7
<212> TYPE: PRT
<213> ORGANISM: Bordetella bronchiseptica

<400> SEQUENCE: 25

Gly Gly Ser Leu Leu Ile Gly
1               5

<210> SEQ ID NO 26
<211> LENGTH: 11
<212> TYPE: PRT
<213> ORGANISM: Bordetella bronchiseptica

<400> SEQUENCE: 26

Val Gly Gly Ser Thr Val Thr Val Thr Phe Pro
1               5                   10

<210> SEQ ID NO 27
<211> LENGTH: 9
<212> TYPE: PRT
<213> ORGANISM: Bordetella bronchiseptica

<400> SEQUENCE: 27

Arg Ala Lys Val Lys Val Asp Phe Pro
1               5

<210> SEQ ID NO 28
<211> LENGTH: 8
<212> TYPE: PRT
<213> ORGANISM: Bordetella bronchiseptica

<400> SEQUENCE: 28

Gly Gly Asp Ile Val Val Thr Gln
1               5

<210> SEQ ID NO 29
<211> LENGTH: 6
<212> TYPE: PRT
<213> ORGANISM: Bordetella bronchiseptica

<400> SEQUENCE: 29

Gly Ala Val Arg Thr His
1               5

<210> SEQ ID NO 30
<211> LENGTH: 8
<212> TYPE: PRT
<213> ORGANISM: Bordetella bronchiseptica

<400> SEQUENCE: 30

Leu Asp Gly Ile Val Ala Arg Phe
1               5

<210> SEQ ID NO 31
<211> LENGTH: 6
<212> TYPE: PRT
<213> ORGANISM: Bordetella bronchiseptica

<400> SEQUENCE: 31

Gly Asp Val Val Ala Gly
1               5

<210> SEQ ID NO 32
<211> LENGTH: 9
<212> TYPE: PRT
<213> ORGANISM: Bordetella bronchiseptica

<400> SEQUENCE: 32

Ser Gly Arg Val Thr Val Ser Gly Lys
1               5

<210> SEQ ID NO 33
<211> LENGTH: 7
<212> TYPE: PRT
<213> ORGANISM: Bordetella bronchiseptica

<400> SEQUENCE: 33

Lys Glu Val Val Ala Gly Pro
1               5

<210> SEQ ID NO 34
<211> LENGTH: 6
<212> TYPE: PRT
<213> ORGANISM: Bordetella bronchiseptica

<400> SEQUENCE: 34

Arg Thr Val Gln Tyr Asp
1               5

<210> SEQ ID NO 35
<211> LENGTH: 9
<212> TYPE: PRT
<213> ORGANISM: Bordetella bronchiseptica

```
<400> SEQUENCE: 35

Phe Thr Val Ala Ser Lys Gly Asp Val
1               5

<210> SEQ ID NO 36
<211> LENGTH: 10
<212> TYPE: PRT
<213> ORGANISM: Bordetella bronchiseptica

<400> SEQUENCE: 36

Pro Ala Gly Pro Ile Arg Val Ser Ala Arg
1               5                   10

<210> SEQ ID NO 37
<211> LENGTH: 6
<212> TYPE: PRT
<213> ORGANISM: Bordetella bronchiseptica

<400> SEQUENCE: 37

Asp His Tyr Leu Asp Ala
1               5

<210> SEQ ID NO 38
<211> LENGTH: 7
<212> TYPE: PRT
<213> ORGANISM: Bordetella bronchiseptica

<400> SEQUENCE: 38

Gly Ala Lys Val Arg Ile Asp
1               5

<210> SEQ ID NO 39
<211> LENGTH: 6
<212> TYPE: PRT
<213> ORGANISM: Bordetella bronchiseptica

<400> SEQUENCE: 39

Tyr Thr Val Thr Ser Thr
1               5

<210> SEQ ID NO 40
<211> LENGTH: 7
<212> TYPE: PRT
<213> ORGANISM: Bordetella bronchiseptica

<400> SEQUENCE: 40

Asp Ile Thr Val Ser Gly Thr
1               5

<210> SEQ ID NO 41
<211> LENGTH: 9
<212> TYPE: PRT
<213> ORGANISM: Bordetella bronchiseptica

<400> SEQUENCE: 41

Arg Arg Thr Val Gln Tyr Asp Asp Arg
1               5

<210> SEQ ID NO 42
<211> LENGTH: 9
<212> TYPE: PRT
<213> ORGANISM: Bordetella bronchiseptica
```

```
<400> SEQUENCE: 42

Leu Arg Pro Val Ala Arg Leu Leu Leu
1               5

<210> SEQ ID NO 43
<211> LENGTH: 9
<212> TYPE: PRT
<213> ORGANISM: Bordetella bronchiseptica

<400> SEQUENCE: 43

Ala Arg Glu Ala Thr Thr Met Val Leu
1               5

<210> SEQ ID NO 44
<211> LENGTH: 10
<212> TYPE: PRT
<213> ORGANISM: Bordetella bronchiseptica

<400> SEQUENCE: 44

Ile Arg Leu Leu Arg Pro Val Ala Arg Leu
1               5                   10

<210> SEQ ID NO 45
<211> LENGTH: 10
<212> TYPE: PRT
<213> ORGANISM: Bordetella bronchiseptica

<400> SEQUENCE: 45

Ala Arg Glu Ala Thr Thr Met Val Leu Lys
1               5                   10

<210> SEQ ID NO 46
<211> LENGTH: 9
<212> TYPE: PRT
<213> ORGANISM: Bordetella bronchiseptica

<400> SEQUENCE: 46

Lys Arg Pro Tyr His Asp Ile Phe Val
1               5

<210> SEQ ID NO 47
<211> LENGTH: 10
<212> TYPE: PRT
<213> ORGANISM: Bordetella bronchiseptica

<400> SEQUENCE: 47

Arg Arg Thr Val Gln Tyr Asp Asp Arg Val
1               5                   10

<210> SEQ ID NO 48
<211> LENGTH: 10
<212> TYPE: PRT
<213> ORGANISM: Bordetella bronchiseptica

<400> SEQUENCE: 48

Gly Pro Val Lys Arg Pro Tyr His Asp Ile
1               5                   10

<210> SEQ ID NO 49
<211> LENGTH: 10
<212> TYPE: PRT
<213> ORGANISM: Bordetella bronchiseptica
```

```
<400> SEQUENCE: 49

Glu Val Ala Thr Asp Ser Ser Gly Arg
1               5

<210> SEQ ID NO 50
<211> LENGTH: 10
<212> TYPE: PRT
<213> ORGANISM: Bordetella bronchiseptica

<400> SEQUENCE: 50

Arg Pro Tyr His Asp Ile Phe Val Pro Val
1               5                   10

<210> SEQ ID NO 51
<211> LENGTH: 9
<212> TYPE: PRT
<213> ORGANISM: Bordetella bronchiseptica

<400> SEQUENCE: 51

Ile Arg Leu Leu Arg Pro Val Ala Arg
1               5

<210> SEQ ID NO 52
<211> LENGTH: 9
<212> TYPE: PRT
<213> ORGANISM: Bordetella bronchiseptica

<400> SEQUENCE: 52

Ala Arg Phe Glu Pro Ala Asn Gly Ala
1               5

<210> SEQ ID NO 53
<211> LENGTH: 9
<212> TYPE: PRT
<213> ORGANISM: Bordetella bronchiseptica

<400> SEQUENCE: 53

Ile Arg Val Ser Ala Arg Gly Pro Arg
1               5

<210> SEQ ID NO 54
<211> LENGTH: 10
<212> TYPE: PRT
<213> ORGANISM: Bordetella bronchiseptica

<400> SEQUENCE: 54

Val Arg Ile Asp Phe Pro Asp Gly Thr Phe
1               5                   10

<210> SEQ ID NO 55
<211> LENGTH: 9
<212> TYPE: PRT
<213> ORGANISM: Bordetella bronchiseptica

<400> SEQUENCE: 55

Val Pro Val Pro Pro Thr Val Glu Val
1               5

<210> SEQ ID NO 56
<211> LENGTH: 10
<212> TYPE: PRT
<213> ORGANISM: Bordetella bronchiseptica
```

```
<400> SEQUENCE: 56

Ala Pro Val Val Pro Gly Ala Asn Gly Val
1               5                   10

<210> SEQ ID NO 57
<211> LENGTH: 10
<212> TYPE: PRT
<213> ORGANISM: Bordetella bronchiseptica

<400> SEQUENCE: 57

Leu Glu Ser Asn Lys Met Phe Ile Tyr Leu
1               5                   10

<210> SEQ ID NO 58
<211> LENGTH: 9
<212> TYPE: PRT
<213> ORGANISM: Bordetella bronchiseptica

<400> SEQUENCE: 58

Gly Arg Pro Gly Asp Thr Ile Arg Val
1               5

<210> SEQ ID NO 59
<211> LENGTH: 9
<212> TYPE: PRT
<213> ORGANISM: Bordetella bronchiseptica

<400> SEQUENCE: 59

Met Arg Thr Asp Gly Asn Ser Gly Val
1               5

<210> SEQ ID NO 60
<211> LENGTH: 9
<212> TYPE: PRT
<213> ORGANISM: Bordetella bronchiseptica

<400> SEQUENCE: 60

Arg Arg Pro Tyr Val Asp Thr Val Ala
1               5

<210> SEQ ID NO 61
<211> LENGTH: 9
<212> TYPE: PRT
<213> ORGANISM: Bordetella bronchiseptica

<400> SEQUENCE: 61

Val Arg Arg Pro Tyr Val Asp Thr Val
1               5

<210> SEQ ID NO 62
<211> LENGTH: 9
<212> TYPE: PRT
<213> ORGANISM: Bordetella bronchiseptica

<400> SEQUENCE: 62

Tyr Arg Ala Thr Ser Asp Gly Asp Val
1               5

<210> SEQ ID NO 63
<211> LENGTH: 9
<212> TYPE: PRT
<213> ORGANISM: Bordetella bronchiseptica
```

<400> SEQUENCE: 63

Val Arg Thr His Pro Gly Thr Gly Val
1               5

<210> SEQ ID NO 64
<211> LENGTH: 10
<212> TYPE: PRT
<213> ORGANISM: Bordetella bronchiseptica

<400> SEQUENCE: 64

Met Arg Thr Asp Gly Asn Ser Gly Val Val
1               5                   10

<210> SEQ ID NO 65
<211> LENGTH: 10
<212> TYPE: PRT
<213> ORGANISM: Bordetella bronchiseptica

<400> SEQUENCE: 65

Val Arg Thr His Pro Gly Thr Gly Val Val
1               5                   10

<210> SEQ ID NO 66
<211> LENGTH: 10
<212> TYPE: PRT
<213> ORGANISM: Bordetella bronchiseptica

<400> SEQUENCE: 66

Asn Arg Val Pro Asn Gly Asp Tyr Pro Val
1               5                   10

<210> SEQ ID NO 67
<211> LENGTH: 10
<212> TYPE: PRT
<213> ORGANISM: Bordetella bronchiseptica

<400> SEQUENCE: 67

Ala Arg Leu Leu Leu Ser Pro Gly Ser Met
1               5                   10

<210> SEQ ID NO 68
<211> LENGTH: 10
<212> TYPE: PRT
<213> ORGANISM: Bordetella bronchiseptica

<400> SEQUENCE: 68

Tyr Arg Leu Glu Ser Asn Lys Met Phe Ile
1               5                   10

<210> SEQ ID NO 69
<211> LENGTH: 9
<212> TYPE: PRT
<213> ORGANISM: Bordetella bronchiseptica

<400> SEQUENCE: 69

Phe Pro Gly Gly Thr Ser Lys Thr Val
1               5

<210> SEQ ID NO 70
<211> LENGTH: 9
<212> TYPE: PRT
<213> ORGANISM: Bordetella bronchiseptica

<400> SEQUENCE: 70

Ala Pro Thr Pro Met Lys Val Thr Ile
1               5

<210> SEQ ID NO 71
<211> LENGTH: 10
<212> TYPE: PRT
<213> ORGANISM: Bordetella bronchiseptica

<400> SEQUENCE: 71

Gly Pro Ser Leu Gly Gly Ser Leu Leu Ile
1               5                   10

<210> SEQ ID NO 72
<211> LENGTH: 10
<212> TYPE: PRT
<213> ORGANISM: Bordetella bronchiseptica

<400> SEQUENCE: 72

Ser Pro Gly Ser Met Thr Tyr Thr Glu Ile
1               5                   10

<210> SEQ ID NO 73
<211> LENGTH: 10
<212> TYPE: PRT
<213> ORGANISM: Bordetella bronchiseptica

<400> SEQUENCE: 73

Val Val Ala Gly Pro Asp Gly Thr Tyr Arg
1               5                   10

<210> SEQ ID NO 74
<211> LENGTH: 10
<212> TYPE: PRT
<213> ORGANISM: Bordetella bronchiseptica

<400> SEQUENCE: 74

Phe Pro Asp Gly Thr Thr Lys Glu Val Val
1               5                   10

<210> SEQ ID NO 75
<211> LENGTH: 10
<212> TYPE: PRT
<213> ORGANISM: Bordetella bronchiseptica

<400> SEQUENCE: 75

Arg Glu Ser Pro Arg Arg Thr Val Gln Tyr
1               5                   10

<210> SEQ ID NO 76
<211> LENGTH: 9
<212> TYPE: PRT
<213> ORGANISM: Bordetella bronchiseptica

<400> SEQUENCE: 76

Phe Pro Asp Gly Thr Thr Lys Glu Val
1               5

<210> SEQ ID NO 77
<211> LENGTH: 9
<212> TYPE: PRT
<213> ORGANISM: Bordetella bronchiseptica

```
<400> SEQUENCE: 77

Ala Ala Leu Leu Ala Ala Ile Lys Leu
1               5

<210> SEQ ID NO 78
<211> LENGTH: 9
<212> TYPE: PRT
<213> ORGANISM: Bordetella bronchiseptica

<400> SEQUENCE: 78

Met Pro Gly Ala Ala Gly Lys Pro Val
1               5

<210> SEQ ID NO 79
<211> LENGTH: 9
<212> TYPE: PRT
<213> ORGANISM: Bordetella bronchiseptica

<400> SEQUENCE: 79

Phe Pro Asp Gly Thr Phe Gly Asp Val
1               5

<210> SEQ ID NO 80
<211> LENGTH: 10
<212> TYPE: PRT
<213> ORGANISM: Bordetella bronchiseptica

<400> SEQUENCE: 80

Val Ala Pro Thr Pro Met Lys Val Thr Ile
1               5                   10

<210> SEQ ID NO 81
<211> LENGTH: 9
<212> TYPE: PRT
<213> ORGANISM: Bordetella bronchiseptica

<400> SEQUENCE: 81

Lys Leu His Asp Pro Asn Tyr Arg Leu
1               5

<210> SEQ ID NO 82
<211> LENGTH: 9
<212> TYPE: PRT
<213> ORGANISM: Bordetella bronchiseptica

<400> SEQUENCE: 82

Asp Ala Trp Thr Lys Gln Thr Leu Leu
1               5

<210> SEQ ID NO 83
<211> LENGTH: 10
<212> TYPE: PRT
<213> ORGANISM: Bordetella bronchiseptica

<400> SEQUENCE: 83

Asp Thr Met Asn Ser Asp Pro Tyr Asn Arg
1               5                   10

<210> SEQ ID NO 84
<211> LENGTH: 9
<212> TYPE: PRT
<213> ORGANISM: Bordetella bronchiseptica
```

```
<400> SEQUENCE: 84

Tyr Arg Leu Glu Ser Asn Lys Met Phe
1               5

<210> SEQ ID NO 85
<211> LENGTH: 10
<212> TYPE: PRT
<213> ORGANISM: Bordetella bronchiseptica

<400> SEQUENCE: 85

Gly Arg Val Thr Val Ser Gly Lys Gly Arg
1               5                   10
```

BORDETELLA OUTER-MEMBRANE PROTEIN ANTIGENS AND METHODS OF MAKING AND USING THE SAME

RELATED APPLICATIONS

This application is a continuation of and claims priority to U.S. patent application Ser. No. 14/498,537, filed Sep. 26, 2014, which is a continuation of and claims priority to U.S. patent application Ser. No. 12/680,823, filed Jul. 16, 2010, now issued as U.S. Pat. No. 8,877,201, which is a 35 U.S.C. §371 national phase application of PCT Application PCT/US2008/012051, filed Oct. 23, 2008, and published in English on Jul. 30, 2009, as International Publication No. WO 2009/094006, and which claims the benefit of U.S. Provisional Patent Application Ser. No. 60/982,513, filed Oct. 25, 2007, the disclosure of each of which is incorporated herein by reference in its entirety.

GOVERNMENT SUPPORT

This invention was made with Government Support under Grant No. NCR-2005-05000 from the USDA. The United States Government has certain rights to this invention.

STATEMENT REGARDING ELECTRONIC FILING OF A SEQUENCE LISTING

A Sequence Listing in ASCII text format, submitted under 37 C.F.R. §1.821, entitled 9151-102_ST25.txt, 38172 bytes in size, generated on Jul. 15, 2010, and filed via EFS-Web, is provided in lieu of a paper copy. This Sequence Listing is hereby incorporated by reference into the specification for its disclosures.

FIELD OF THE INVENTION

The present invention concerns antigens, formulations thereof, and methods of using the same.

BACKGROUND OF THE INVENTION

*Bordetellae* are Gram-negative bacteria that colonize the respiratory tracts of humans and animals. *Bordetella bronchiseptica* and *Bordetella pertussis* are well-adapted pathogens of the human and animal respiratory tract, respectively. *Bordetella pertussis* infects only humans and causes the acute respiratory disease known as whooping cough. It is estimated that 20-30% of adolescents and adults who have chronic cough lasting for more than one week are infected with *B. pertussis*. The current acellular vaccines, although effective against severe symptoms, are not particularly effective in preventing the carrier state. Adult and adolescent carriers harboring *B. pertussis* in the nasopharynx are responsible for the familial transmission of the bacteria to infants and young children, in whom the disease is severe and sometimes lethal. Thus, the continued presence of *B. pertussis* and *B. parapertussis* and the resurgence of pertussis despite widespread vaccinations, make the development of efficacious vaccines a top priority.

*B. bronchiseptica* has a broad host range infecting a variety of animals. It typically establishes asymptomatic infections but can cause atrophic rhinitis in pigs, kennel cough in dogs, snuffles in rabbits and bronchopneumonia in guinea pigs. Animals continue to be carriers of *B. bronchiseptica* despite vaccinations and frequently shed bacteria resulting in outbreaks among herds. Since *B. bronchiseptica* can cause respiratory disease in immunocompromized patients, vaccination of pets and food-producing animals with attenuated *B. bronchiseptica* may pose health risks to these patients through zoonotic transmission. Thus, there is a need to develop acellular vaccines for immunizing animals.

SUMMARY OF THE INVENTION

This invention is based upon our identification of a gene, designated by us as BcfA (*Bordetella* colonization factor A) by a bioinformatics approach. We produced and purified BcfA-T7-tagged fusion protein from *E. coli*, and have raised anti-sera against the purified protein in rats. Western-blotting with anti-BcfA antibody indicated that BcfA is localized to the outer membrane and that it is expressed during *Bordetella* infection of rats. By intranasal infection of rats, we have shown that BcfA plays an important role in respiratory colonization of *B. bronchiseptica*. We have also found that BcfA is expressed in recent clinical isolates of *B. pertussis* from human patients. Pilot experiments conducted in the laboratory also provide evidence that anti-serum against BcfA is able to protect mice against subsequent challenge with *B. bronchiseptica*. These data indicate that BcfA is useful as a vaccine and that anti-BcfA serum has a protective effect in animals.

A first aspect of the invention is an isolated protein or peptide selected from the group consisting of *Bordetella* colonization factor A (BcfA) protein and antigenic fragments thereof. In some embodiments, the BcfA protein has the sequence of SEQ ID NO:2. In some embodiments, the protein or peptide is an antigenic fragment of BcfA from 20 to 500 amino acids in length. In some embodiments, the protein or peptide is an antigenic fragment of BcfA having the sequence given herein as SEQ ID NO:3 or an antigenic fragment comprising 10 or more contiguous amino acids thereof.

A further aspect of the invention is an isolated nucleic acid that encodes a protein or peptide as described herein. The nucleic acid may in some embodiments be operatively associated with a promoter, and in some embodiments may be in a host cell that contains the nucleic acid and expresses the encoded protein or peptide.

A further aspect of the invention is a method of producing an immune response in a mammalian subject in need thereof, comprising administering the subject a protein or peptide as described herein in an amount effective to produce an immune response in that subject (e.g., a protective immune response to *Bordetella* infection, such as a *Bordetella bronchiseptica* or *Bordetella pertussis* infection).

A further aspect of the present invention is a composition comprising a protein or peptide as described herein in a pharmaceutically acceptable carrier.

A further aspect of the invention is an isolated antibody (e.g., a monoclonal antibody or polyclonal antibody) that binds to BcfA protein (e.g., a protein of SEQ ID NO:2). In some embodiments the antibody may be coupled to a solid support or a detectable group.

A further aspect of the present invention is a composition comprising an antibody as described herein in a pharmaceutically acceptable carrier.

A further aspect of the present invention is a method of treating a mammalian subject for a *Bordetella* infection (e.g., a *Bordetella bronchiseptica* or *Bordetella pertussis* infection), comprising administering the subject an antibody as described herein in a treatment effective amount.

A further aspect of the invention is a method of detecting *Bordetella* (e.g., *Bordetella bronchiseptica* or *Bordetella pertussis*) in a biological sample, comprising: contacting the sample to an antibody as described herein; and then detecting the presence or absence of specific binding of the antibody to the sample, the presence of specific binding to the sample indicating the presence of *Bordetella* in the sample.

A still further aspect of the invention is the use of a protein, peptide, or antibody as described herein for the preparation of a medicament for carrying out a method of treatment as described herein.

BRIEF DESCRIPTION OF THE DRAWINGS

FIG. 1 shows the nucleotide sequence encoding BcfA protein.

FIG. 2A shows the amino acid sequence of full-length BcfA. FIG. 2B shows the predicted 508 amino acid residue extracellular domain of BcfA. FIGS. 2C-2L show fragments of the extracellular domain of BcfA.

DETAILED DESCRIPTION OF THE INVENTION

Figure 3:
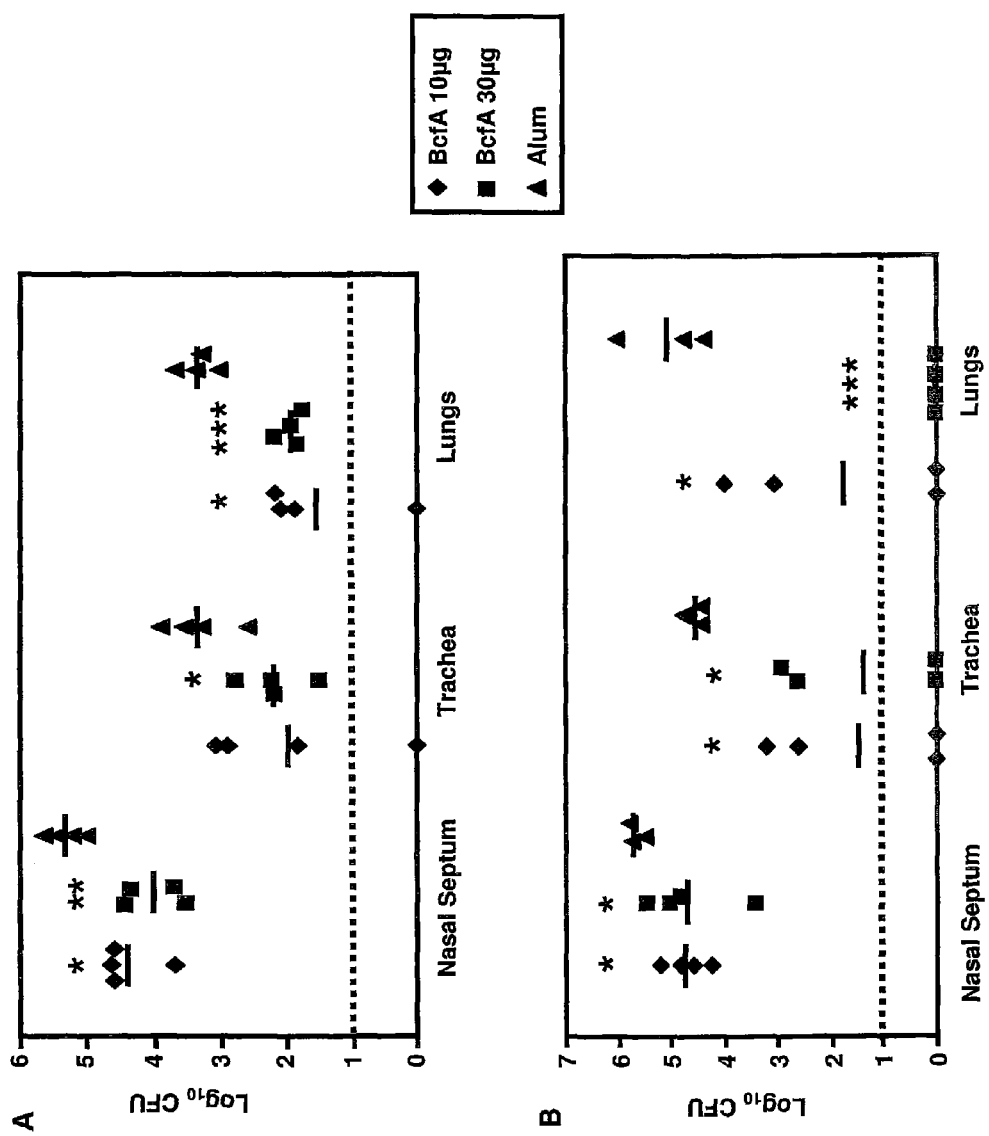
FIG. 3 shows that Immunization with BcfA protects mice against *B. bronchiseptica* challenge.

Subjects to be treated by the methods of the present invention are generally mammalian subjects, including but not limited to human, monkey, chimpanzee, ape, dog, cat, pig, rabbit, goat, cow, cattle, horse, etc. Subjects may be male or female and may be any age including neonate, infant, juvenile, adolescent, adult, and geriatric subjects.

"Antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26, 403-11 (1989). The antibodies may be recombinant monoclonal antibodies, for example produced according to the methods disclosed in Reading U.S. Pat. No. 4,474,893, or Cabilly et al., U.S. Pat. No. 4,816,567. The antibodies may be humanized or chimeric antibodies. The antibodies may also be chemically constructed according to methods such as disclosed in Segal et al., U.S. Pat. No. 4,676,980.

"Antigenic fragment" of a protein (e.g., BcfA) as used herein is any portion of the protein that, when administered in accordance with the methods described herein, elicits, in a subject, an immune response that is either a fragment-specific or specific for the protein from which the fragment was obtained. The immune response can be either a humoral or a cell-mediated response. Antigenic fragments are known. See, e.g., U.S. Pat. No. 7,101,987; see also U.S. Pat. Nos. 7,270,816; 7,211,411; 7,163,685; and 7,151,082. Antigenic fragments can be of any suitable length (e.g., from 10, 12 or 20 contiguous amino acids up to 50, 100 or 200 contiguous amino acids or more) and generated by known techniques such as epitope mapping. (e.g., a fragment that includes an epitope region as described below).

1. Antigens

The present invention includes *B. bronchiseptica* compositions composed of one or more *B. bronchiseptica* antigens against which it is desired to generate an immune response. The use of bacterial antigens in the production of antigen compositions and vaccines is well-known in the art and described in, for example, U.S. Pat. No. 7,255,867.

Compositions of the invention may be composed of BcfA (SEQ ID NO:2), the extracellular domain of BcfA (SEQ ID NO:3), or fragments or epitopes thereof. The instant vaccine can be a monovalent vaccine or multi-valent vaccine. Multi-valent vaccines generally include more than one type of antigen and can be produced by mixing a number of different antigens.

The instant antigen(s) can be made using any conventional synthetic or recombinant means. The amino acid sequence of an antigen for use in the invention can be modified to include non-naturally occurring amino acids or to increase the stability of the compound. When the antigen is produced by synthetic means, such amino acids may be introduced during production. The antigen may also be modified following either synthetic or recombinant production.

The antigen for use in the invention may also be produced using D-amino acids. In such cases, the amino acids will be linked in reverse sequence in the C to N orientation. This is conventional in the art for producing such peptides. A number of side chain modifications are also known in the art and may be made to the side chains of the antigen for use in the present invention. Such modifications include, for example, modifications of amino acids by reductive alkylation by reaction with an aldehyde followed by reduction with $NABH_4$, amidination with methylacetimidate or acylation with acetic anhydride.

An antigen for use in the invention can be produced in large scale following purification by high pressure liquid chromatography (HPLC) or other techniques after recombinant expression as described herein.

Polynucleotides to produce an antigen for use in the invention can include DNA or RNA. They may also be polynucleotides which include within them synthetic or modified nucleotides. A number of different types of modifications to polynucleotides are known in the art. These include methylphosphate and phosphorothioate backbones, addition of acridine or polylysine chains at the 3' and/or 5' ends of the molecule. Although the techniques mentioned herein are generally well-known in the art, reference may be made in particular to Sambrook and Russell (2001) *Molecular Cloning: A Laboratory Manual*, $3^{rd}$ Edition, CSHL Press.

An antigen for use in the present invention can be produced by recombinant means by providing a polynucleotide encoding the antigen and, where appropriate, encoding any desired flanking sequences under the control of a promoter and other required sequences. Such a polynucleotide is generally provided in the form of an expression vector.

Such vectors can be transformed into a suitable host cell to provide for expression of an antigen of the invention. Thus, an antigen for use according to the invention can be obtained by cultivating a host cell transformed or transfected with an expression vector as described above under conditions to provide for expression of the antigen, and recovering the expressed antigen.

The vectors may be, for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Promoters and other expression regulation signals may be selected to be compatible with the host cell for which the expression vector is designed.

Host cells transformed (or transfected) with the polynucleotides or vectors for the replication and expression of polynucleotides of the invention will be chosen to be compatible with the said vector and preferably will be bacterial, e.g., *E. coli*. Alternatively they may be cells of a human or animal cell line such as CHO or COS cells, or yeast or insect cells. The cells may also be cells of a non-human animal such as a sheep or rabbit or plant cells.

2. Antigen Compositions

An antigen composition of the present invention can also include one or more adjuvants. Adjuvants for use in the production of antigenic compositions such as vaccines are well-known and routinely employed by the skilled artisan. See, e.g., U.S. Pat. No. 7,183,402. For example, adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211, WO 96/06627, and WO 95/34323. Other adjuvants, such as a bacterial monophosphoryl lipid A (MPLA) of, e.g., *E. coli, Salmonella minnesota, Salmonella typhimurium*, or *Shigella flexneri*; saponins, or polylactide glycolide (PLGA) microspheres, are also be used in mucosal administration.

Adjuvants useful for both mucosal and parenteral administrations include polyphosphazene (WO 95/02415), DC-chol (3 b-(N—(N',N'-dimethyl aminomethane)-carbamoyl) cholesterol (U.S. Pat. No. 5,283,185 and WO 96/14831) and QS-21 (WO 88/09336).

The compositions of the present invention may be administered by any suitable route. The compositions can be formulated for delivery by a mucosal, parenteral or transdermal route. Mucosal delivery routes include nasal, oral and oropharangeal routes, whereas parenteral routes include intramuscular, intraperitoneal, or subcutaneous injection.

Suitable binders and carriers may also be introduced into the present composition depending on the type of formulation that is provided. Oral formulations typically may include excipients such as, for example, pharmaceutical grades of mannitol, lactose, starch, sodium saccharine, cellulose, and magnesium carbonate. In some embodiments, vaccination is carried out by intranasal delivery of a liquid or spray.

The compositions are administered in a manner compatible with the dosage formulation in such an amount as will be prophylactically effective. The quantity to be administered depends on a number of factors. These include the subject to be treated, capacity of the subject's immune system to synthesize antibodies and the degree of protection desired. Precise amounts of active ingredient required to be administered may depend on the judgment of the practitioner. In general, the dose per subject may be 5 µg, 50 µg, or 250 µg, up to 10 mg or 100 mg, per dose.

The compositions may be given in a single dose schedule or preferably in a multiple-dose schedule. A multiple-dose schedule is one in which a primary course of vaccination may be with 1 or 2 up to 5 or 10 separate doses, followed by other doses given at subsequent time intervals required to maintain and/or reinforce the immune response, for example, at 1 to 4 months for a second dose and if needed, a subsequent dose(s) after several months.

3. Antibodies

Polyclonal antibodies used to carry out the present invention may be produced by immunizing a suitable animal (e.g., rabbit, goat, etc.) with an antigen to which a monoclonal antibody to BcfA binds, collecting immune serum from the animal, and separating the polyclonal antibodies from the immune serum, in accordance with known procedures.

Monoclonal antibodies used to carry out the present invention may be produced in a hybridoma cell line according to the technique of Kohler and Milstein, *Nature* 265, 495-97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity. Monoclonal Fab fragments may be produced in *Escherichia coli* by recombinant techniques known to those skilled in the art. See, e.g., W. Huse, *Science* 246, 1275-81 (1989).

Antibodies specific to BcfA can also be obtained by phage display techniques known in the art.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." Applicants specifically intend that the disclosures of all U.S. Patent references cited herein be incorporated herein by reference in their entirety.

Antibodies as described herein may be conjugated to a solid support suitable for a diagnostic assay (e.g., beads, plates, slides or wells formed from materials such as latex or polystyrene) in accordance with known techniques, such as precipitation. Antibodies as described herein may likewise be conjugated to detectable groups such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques. The term "antigenic equivalents" as used herein, refers to proteins or peptides which bind to an antibody which binds to the protein or peptide with which equivalence is sought to be established. Antibodies which are used to select such antigenic equivalents are referred to as "selection antibodies" herein.

4. Utility

Antigens of the present invention (BcfA and fragments thereof) and formulations of such antigens are useful for producing an immune response against said antigen in a mammalian subject. Such an immune response is useful for the production of antibodies, which antibodies can be used for diagnostic purposes (in detecting the presence of *Bordetella*) or for therapeutic purposes in treating *Bordetella* by passive immunity as described herein.

Antigens of the present invention are also useful as vaccines for providing protective immunity in mammalian subjects against *Bordetella* infection.

Example 1

Passive Immunization

Groups of five C57/BL6 mice were separately injected intraperitoneally with 200 µl of sera harvested from wild-type inoculated rats, BcfA-specific polyclonal serum, pre-immune sera or sterile phosphate-buffered saline (PBS). Three to four hours after inoculation, these mice were intranasally challenged with $5 \times 10^5$ colony forming units (cfus) of wild-type *B. bronchiseptica* strain RB50 in a 25 µl droplet. Seven days post-inoculation, mice were sacrificed and trachea, nasal septum and lungs were harvested in sterile PBS and homogenized. Colonization of these organs was quantified by plating different dilutions of the homogenate in BG blood plates containing 50 µg/ml of streptomycin and subsequent colony counting. The results of this analysis indicated that anti-serum raised against BcfA was able to protect mice against subsequent challenge with *B. bronchiseptica*.

Example 2

BcfA Epitopes

The purified BcfA protein migrates in an SDS-polyacrylamide gel at a mobility corresponding to ≈100 kDa, which is consistent with the annotated length (969 amino acids; FIG. 2A) of the BcfA open reading frame. BcfA displays homology to other bacterial proteins including BipA from *Bordetella*, invasins from *Yersinia*, and intimins from enteropathogenic *E. coli*. Based on the known structure of these proteins, the C-terminal 508 amino acid residues of BcfA are expected to encompass the extracellular region of BcfA and thus will interact with the immune system. Accordingly, amino acid residues 461-969 of BcfA (SEQ ID NO:3; FIG. 2B), or one or more fragments thereof, are expected to elicit an immune response against *B. bronchiseptica*. Exemplary fragments of BcfA are shown in FIGS. 2C-2L.

Additional fragments of BcfA include antigenic regions of the BcfA extracellular domain as well as fragments expected to bind to major histocompatibility complex (MHC) class I and MHC class II molecules. Accordingly, the amino acid sequence of the extracellular region of BcfA was analyzed using two independent web-based algorithms that predict antigenic sites in proteins (Table 1) and potential binding to MHC class I and MHC class II molecules (Table 2).

Multiple peptides within the extracellular region of BcfA were predicted to be antigenic and exhibit high binding affinity for human HLA molecules (Table 3).

TABLE 1

| Predicted Epitope | SEQ ID NO: | Location | Antigenic Score[1] |
|---|---|---|---|
| GDYPVTLVLED | 14 | 443 | 1.200 |
| GGPVKRPYHDIFVPVPPTVEVATD | 15 | 165 | 1.179 |
| APTVVLHT | 16 | 91 | 1.165 |

TABLE 1-continued

| Predicted Epitope | SEQ ID NO: | Location | Antigenic Score[1] |
|---|---|---|---|
| QTLLGGKIRLLRPVARLLLSP | 17 | 350 | 1.162 |
| SGVVTVTGY | 18 | 277 | 1.143 |
| PQTAALLAAIKLHDPN | 19 | 402 | 1.137 |
| GKAPVVPGANGV | 20 | 474 | 1.128 |
| GKPVRRPYVDTVAPTPMKVTID | 21 | 248 | 1.119 |
| GTGVVTVT | 22 | 11 | 1.110 |
| ASGPIVAIA | 23 | 57 | 1.108 |
| TMVLKVTGS | 24 | 463 | 1.106 |
| GGSLLIG | 25 | 495 | 1.095 |
| VGGSTVTVTFP | 26 | 287 | 1.093 |
| RAKVKVDFP | 27 | 200 | 1.092 |
| GGDIVVTQ | 28 | 233 | 1.089 |
| GAVRTH | 29 | 4 | 1.086 |
| LDGIVARF | 30 | 387 | 1.086 |
| GDVVAG | 31 | 37 | 1.081 |
| SGRVTVSGK | 32 | 188 | 1.079 |
| KEVVAGP | 33 | 127 | 1.078 |
| RTVQYD | 34 | 76 | 1.078 |
| FTVASKGDV | 35 | 47 | 1.073 |
| PAGPIRVSAR | 36 | 321 | 1.068 |
| DHYLDA | 37 | 341 | 1.052 |
| GAKVRID | 38 | 24 | 1.051 |
| YTVTST | 39 | 312 | 1.050 |
| DITVSGT | 40 | 149 | 1.037 |

Location is the position of the first residue. [1]Score obtained using the Antigenic program which employs the method of Kolaskar and Tongaonkar (1990). FEBS Letters 276: 172-174.

TABLE 2

| Predicted Epitope | SEQ ID NO: | Location | HLA Molecule | BIMAS Score[1,2] |
|---|---|---|---|---|
| RRTVQYDDR | 41 | 75 | HLA-B_2705 | 3000 |
| LRPVARLLL | 42 | 360 | HLA-B_2705 | 2000 |
| AREATTMVL | 43 | 458 | HLA-B_2705 | 2000 |
| IRLLRPVARL | 44 | 357 | HLA-B_2705 | 2000 |
| AREATTMVLK | 45 | 458 | HLA-B_2705 | 2000 |
| KRPYHDIFV | 46 | 166 | HLA-B_2705 | 1800 |
| RRTVQYDDRV | 47 | 75 | HLA-B_2705 | 1800 |
| GPVKRPYHDI | 48 | 163 | HLA-B_5102 | 1320 |
| EVATDSSSGR | 49 | 181 | HLA-A68.1 | 1200 |

TABLE 2-continued

| Predicted Epitope | SEQ ID NO: | Location | HLA Molecule | BIMAS Score[1,2] |
|---|---|---|---|---|
| RPYHDIFVPV | 50 | 167 | HLA-B_5102 | 1100 |
| IRLLRPVAR | 51 | 357 | HLA-B_2705 | 1000 |
| ARFEPANGA | 52 | 392 | HLA-B_2705 | 1000 |
| IRVSARGPR | 53 | 325 | HLA-B_2705 | 1000 |
| VRIDFPDGTF | 54 | 27 | HLA-B_2705 | 1000 |
| VPVPPTVEV | 55 | 174 | HLA-B_5102 | 660 |
| APVVPGANGV | 56 | 476 | HLA-B_5102 | 660 |
| LESNKMFIYL | 57 | 420 | HLA-B60 | 640 |
| GRPGDTIRV | 58 | 111 | HLA-B_2705 | 600 |
| MRTDGNSGV | 59 | 271 | HLA-B_2705 | 600 |
| RRPYVDTVA | 60 | 252 | HLA-B_2705 | 600 |
| VRRPYVDTV | 61 | 251 | HLA-B_2705 | 600 |
| YRATSDGDV | 62 | 223 | HLA-B_2705 | 600 |
| VRTHPGTGV | 63 | 6 | HLA-B_2705 | 600 |
| MRTDGNSGVV | 64 | 271 | HLA-B_2705 | 600 |
| VRTHPGTGVV | 65 | 6 | HLA-B_2705 | 600 |
| NRVPNGDYPV | 66 | 438 | HLA-B_2705 | 600 |
| ARLLLSPGSM | 67 | 364 | HLA-B_2705 | 600 |
| YRLESNKMFI | 68 | 418 | HLA-B_2705 | 600 |
| FPGGTSKTV | 69 | 207 | HLA-B_5102 | 586 |
| APTPMKVTI | 70 | 260 | HLA-B_5101 | 484 |
| GPSLGGSLLI | 71 | 491 | HLA-B_5102 | 484 |
| GPSLGGSLLI | 71 | 491 | HLA-B_5101 | 440 |
| SPGSMTYTEI | 72 | 369 | HLA-B_5101 | 440 |
| GPVKRPYHDI | 48 | 163 | HLA-B_5101 | 440 |
| APTPMKVTI | 70 | 260 | HLA-B_5102 | 440 |
| SPGSMTYTEI | 72 | 369 | HLA-B_5102 | 440 |
| VVAGPDGTYR | 73 | 129 | HLA-A68.1 | 400 |
| FPGGTSKTV | 69 | 207 | HLA-B_5101 | 381 |
| FPDGTTKEVV | 74 | 121 | HLA-B_5101 | 381 |
| RESPRRTVQY | 75 | 71 | HLA-B_4403 | 360 |
| FPDGTTKEV | 76 | 121 | HLA-B_5101 | 346 |
| AALLAAIKL | 77 | 405 | HLA-B_5102 | 330 |
| MPGAAGKPV | 78 | 243 | HLA-B_5101 | 315 |
| FPDGTFGDV | 79 | 31 | HLA-B_5101 | 315 |
| VAPTPMKVTI | 80 | 259 | HLA-B_5101 | 315 |
| KLHDPNYRL | 81 | 412 | HLA-A_0201 | 307 |
| DAWTKQTLL | 82 | 345 | HLA-B_5102 | 303 |
| DTMNSDPYNR | 83 | 430 | HLA-A68.1 | 300 |
| YRLESNKMF | 84 | 418 | HLA-B_2705 | 300 |
| GRVTVSGKGR | 85 | 103 | HLA-B_2705 | 300 |

Location is the position of the first residue. [1]Score obtained using the BIMAS program developed by Parker, et al. (1994) J. Immunol. 152: 163, which provides the rank potential of 8-mer, 9-mer, or 10-mer peptides based on a predicted half-time of dissociation to HLA class I molecules.
[2]Minimum scores 300 on the BIMAS site were used.

TABLE 3

| Predicted Epitope | SEQ ID NO: | Location | Antigenic Score | BIMAS Score |
|---|---|---|---|---|
| RTVQYD | 34 | 76 | 1.179 | |
| RRTVQYDDR | 41 | 75 | | |
| RRTVQYDDRV | 47 | 75 | | 1800 |
| GGPVKRPYHDIFVPVPPTVEVATD | 15 | 165 | 1.179 | |
| KRPYHDIFV | 46 | 166 | | 1800 |
| RPYHDIFVPV | 50 | 167 | | |
| VPVPPTVEV | 55 | 174 | | |
| GKPVRRPYVDTVAPTPMKVTID | 21 | 248 | 1.119 | |
| VRRPYVDTV | 61 | 251 | | |
| RRPYVDTVA | 60 | 252 | | |
| VAPTPMKVTI | 80 | 259 | | |
| APTPMKVTI | 70 | 260 | | 315 |
| QTLLGGKIRLLRPVARLLLSP | 17 | 350 | 1.162 | |
| IRLLRPVARL | 44 | 357 | | |
| IRLLRPVAR | 51 | 357 | | |
| LRPVARLLL | 42 | 360 | | 2000 |
| PQTAALLAAIKLHDPN | 19 | 402 | 1.137 | |
| AALLAAIKL | 77 | 405 | | 330 |
| GKAPVVPGANGV | 20 | 474 | 1.128 | |
| APVVPGANGV | 56 | 476 | | 660 |

Example 3

Active Immunization

FIG. 3 shows that Immunization with BcfA protects mice against *B. bronchiseptica* challenge. Mice were immunized intraperitoneally at 0 and 3 weeks with either 10 or 30 μg of BcfA adsorbed to alum or alum only. One week after the second immunization, mice were intranasally challenged with 5×10⁵ CFU or RB50 in a 25 μl volume. Mice were sacrificed at 1 day (FIG. 3A) and 6 days (FIG. 3B) postchallenge and the number of CFU was determined in the nasal septum, trachea and lungs. Individual symbols represent a single mouse. The dashed line represents the lower limits of CFU detection. Black bars represent mean colonization of respective groups. A statistical analysis was carried out using an unpaired two-tailed Student t test. The asterisks indicate the range of the different P values (one asterisk, ≤0.05; two asterisks, ≤0.005 and three asterisks, ≤0.0005).

The foregoing is illustrative of the present invention, and is not to be construed as limiting thereof. The invention is defined by the following claims, with equivalents of the claims to be included therein.

That which is claimed is:

1. A method of producing an immune response in a mammalian subject in need thereof, comprising administering to said subject an isolated protein or peptide comprising (i) the *Bordetella* colonization factor A (BcfA) protein of SEQ ID NO: 2 or (ii) and antigenic fragments thereof comprising 20 or more contiguous amino acids thereof, in an amount effective to produce an immune response.

2. The method of claim 1, wherein said protein or peptide is an antigenic fragment of BcfA having the sequence given herein as SEQ ID NO: 3 or an antigenic fragment comprising 20 or more contiguous amino acids thereof.

3. The method of claim 1, wherein said administering further comprises an adjuvant.

4. The method of claim 1, wherein said administering delivers said BcfA protein or peptide by a mucosal route.

5. The method of claim 1, wherein said administering delivers said BcfA protein or peptide by a parenteral route.

6. The method of claim 1, wherein said administering delivers said BcfA protein or peptide by a transdermal route.

7. The method of claim 1, wherein said administering delivers said effective amount of BcfA protein or peptide in a single dose schedule.

8. The method of claim 1, wherein said administering delivers said effective amount of BcfA protein or peptide in a multiple dose schedule.

9. A method of producing an immune response in a mammalian subject in need thereof, comprising administering to said subject an isolated *Bordetella* colonization factor A (BcfA) peptide comprising an antigenic fragment of 20 or more contiguous amino acids of SEQ ID NO: 2 in an amount effective to produce an immune response.

10. The method of claim 9, wherein said administering further comprises an adjuvant.

11. The method of claim 9, wherein said administering delivers said BcfA peptide antigenic fragment by a mucosal route.

12. The method of claim 9, wherein said administering delivers said BcfA peptide antigenic fragment by a parenteral route.

13. The method of claim 9, wherein said administering delivers said BcfA peptide antigenic fragment by a transdermal route.

14. The method of claim 9, wherein said administering delivers said effective amount of BcfA peptide antigenic fragment in a single dose schedule.

15. The method of claim 9, wherein said administering delivers said effective amount of BcfA peptide antigenic fragment in a multiple dose schedule.

* * * * *